(12) United States Patent
Lee

(10) Patent No.: US 11,931,330 B2
(45) Date of Patent: Mar. 19, 2024

(54) COMPOSITION FOR PROMOTING SKELETAL MUSCLE ACTIVITY VIA INDUCTION OF MITOCHONDRIAL BIOGENESIS COMPRISING OF AZELAIC ACID AS AN ACTIVE INGREDIENT

(71) Applicant: Korea University Research and Business Foundation, Seoul (KR)

(72) Inventor: Sung-Joon Lee, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 17/010,153

(22) Filed: Sep. 2, 2020

(65) Prior Publication Data

US 2020/0397733 A1  Dec. 24, 2020

Related U.S. Application Data

(63) Continuation-in-part of application No. 16/278,899, filed on Feb. 19, 2019, now abandoned.

(30) Foreign Application Priority Data

Feb. 20, 2018   (KR) .......................... 10-2018-0020070

(51) Int. Cl.
  *A61K 31/20*    (2006.01)
  *A61P 21/00*    (2006.01)

(52) U.S. Cl.
  CPC .............. *A61K 31/20* (2013.01); *A61P 21/00* (2018.01)

(58) Field of Classification Search
  CPC ................................ A61K 31/20; A61P 21/00
  USPC ....................................................... 514/574
  See application file for complete search history.

(56) References Cited

U.S. PATENT DOCUMENTS 8,906,390 B2 * 12/2014 Khan ...................... A61P 25/16
                                                    424/283.1
2012/0251525 A1 * 10/2012 Streeper ..................... A61P 9/10
                                                    424/130.1

FOREIGN PATENT DOCUMENTS

| CN | 1192134 A | 9/1998 | |
|---|---|---|---|
| KR | 10-2004-0010681 A | 1/2004 | |
| KR | 10-2012-0064604 A | 6/2012 | |
| KR | 10-2013-0101515 A | 9/2013 | |
| KR | 10-2015-0028958 A | 3/2015 | |
| WO | WO-9212960 A2 * | 8/1992 | ............ A23L 33/12 |
| WO | WO-2018128479 A1 * | 7/2018 | ............ A23K 20/10 |

OTHER PUBLICATIONS

Fenwick, Gruffydd Roger et al., "The Genus Allium—Part 1", Critical Reviews in Food Science & Nutrition, vol. 22, Issue 3, 1985 (pp. 199-271).
Zhang, Yi et al., "Progress of Preclinical Pharmaceutical Research on Azelaic Acid," China pharmaceutical Industry, vol. 16, No. 18, Sep. 20, 2007 (5 pages in English, 2 pages in Chinese).
Thanh Thach, Trung et al., "Molecular determinants of the olfactory receptor Olfr544 activation by azelaic acid", Biochemical and Biophysical Research Communications, 485.2, Feb. 20, 2017, (pp. 241-248).
United States Office Action dated Aug. 5, 2019 in related application, U.S. Appl. No. 16/279,015 (10 pages in English).
United States Office Action dated May 6, 2019 in related application, U.S. Appl. No. 15/861,239 (24 pages in English).
United States Office Action dated Nov. 18, 2019 in related application, U.S. Appl. No. 15/861,239 (17 pages in English).
Wu et al., "Olfactory receptor 544 reduces adiposity by steering fuel preference toward fats," The Journal of Clinical Investigation, vol. 127, Issue 11 (12 pages in English).
Muthulakshmi et al., "Protective effects of azelaic acid against high-fat diet-induced oxidative stress in liver, kidney and heart of C57BL/6J mice"; 2013; Mol Cell Biochem.; 377:23-33 (Year: 2013).
Deeks et al., "Rosiglitazone a Review of its Use in Type 2 Diabetes Mellitus," Drugs, 67:2747-2779 (2007).
Carmona et al., "Fenofibrate Prevents Rosiglitazone-Induced Body Weight Gain in ob/ob Mice," International Journal of Obesity, 29:864-871 (2005).
Chaput et al., "Fenofibrate and Rosiglitazone Lower Serum Triglycerides with Opposing Effects on Body Weight," Biochemical and Biophysical Research Communications, 271:445-450, 2000.
Kahn et al., "Glycemic Durability of Rosiglitazone, Metformin, or Glyburide Monotherapy," The New England Journal of Medicine, 2427-2443, Dec. 7, 2006.
Muthulakshmi et al., "Gene Expression Profile of High-Fat Diet-Fed C57BL/6J Mice: In Search of Potential Role of Azelaic Acid," J. Physiol. Biochem, 71 (2015) 29-42.
Wilson-Fritch et al., "Mitochondrial remodeling in adipose tissue associated with obesity and treatment with rosiglitazone," The Journal of Clinical Investigation, vol. 114, No. 9, Nov. 1, 2004, pp. 1281-1289.

(Continued)

Primary Examiner — Yong S. Chong
(74) Attorney, Agent, or Firm — NSIP Law

(57) ABSTRACT

A composition for promoting mitochondrial biogenesis includes an effective amount of an azelaic acid or a pharmaceutically acceptable salt thereof as an active ingredient. Azelaic acid, which is a compound mainly contained in cereals and natural products has the advantage of no or little side effects, and induces mitochondrial autophagy and mitochondrial DNA synthesis in cells, thereby having activity of increasing mitochondrial density. Therefore, azelaic acid can be used for the treatment of mitochondrial dysfunction-associated disease caused by the failure of homeostasis control of the mitochondria, for example, mitochondrial activity or the decrease in the number of mitochondria. In addition, azelaic acid can be provided to reinforce a muscle function and prevent muscle aging using the activity, and to be effectively used in a food material, a pharmaceutical composition, and health functional foods for treating mitochondrial dysfunction-associated disease, reinforcing a muscle function, or preventing muscle aging.

5 Claims, 20 Drawing Sheets

(56) References Cited

OTHER PUBLICATIONS

Perreault et al., "PPAR-delta Agonism for the Treatment of Obesity and Associated Disorders: Challenges and Opportunities," PPAR Research, vol. 2008, Jan. 1, 2008, pp. 1-9.
Supplementary European Search Report, Application No. EP16821568.9; dated Jan. 29, 2019.
Zhuang et al., "Evaluating cell-surface expression and measuring activation of mammalian odorant receptors in heterologous cells," Nature Protocols, vol. 3, No. 9, pp. 1402-1413, Aug. 14, 2008.
Wu et al., "Activation of OR1A1 suppresses PPAR-γ expression by inducing HES-1 in cultured hepatocytes," The International Journal of Biochemistry & Cell Biology, 64 (2015) 75-80.
Muthulakshmi et al., "Efficacy of azelaic acid on hepatic key enzymes of carbohydrate metabolism in high fat diet induced type 2 diabetic mice," Biochimie, vol. 95, No. 6 (Feb. 28, 2013), pp. 1239-1244, XP028593691.
Kang et al., "Olfactory receptor Olfr544 responding to azelaic acid regulates glucagon secretion in α-cells of mouse pancreatic islets," Biochemical and Biophysical Research Communications, 460, No. 3 (Mar. 21, 2015) pp. 616-621, XP029156356.
Green et al., "An Established Preadipose Cell Line and its Differentiation in Culture," Cell, vol. 5, pp. 19-27 (May 1975).
Green et al., "An Established Pre-Adipose Cell Line and its Differentiation in Culture," Cell, vol. 3, pp. 127-133 (Oct. 1974).
Atanasov et al., "Honokiol: a non-adipogenic PPARγ agonist from nature", Biochimica et Biophysica Acta, 1830 (2013) pp. 4813-4819.
Chinese Office Action dated Mar. 16, 2020 in Chinese Patent Application No. 201680045618.7 (6 pages in English, 5 pages in Chinese).
Heo, Jun-Won, et al. "Effects of exercise on obesity-induced mitochondrial dysfunction in skeletal muscle." *The Korean Journal of Physiology & Pharmacology* 21.6 (Aug. 23, 2017): pp. 567-577.
Shepard, Blythe D., et al. "A renal olfactory receptor aids in kidney glucose andling." *Scientific reports* 6.1 (Oct. 14, 2016): pp. 1-13.
Goldgar, Constance, et al. "Treatment options for acne rosacea." *American Family Physician* 80.5 (Sep. 1, 2009): pp. 461-468.
Litvinov, Dmitry, et al. "Anti-atherosclerotic actions of azelaic acid, an end product of linoleic acid peroxidation, in mice." *Atherosclerosis* 209.2 (Apr. 1, 2011): pp. 449-454.
Pan, Yunbao, et al. "Azelaic acid exerts antileukemic activity in acute myeloid leukemia." *Frontiers in Pharmacology* vol. 8 Article 359 (Jun. 12, 2017): pp. 1-9.
Kwak, Soo Heon, et al. "Mitochondrial metabolism and diabetes." *Journal of diabetes investigation* 1.5 (Oct. 5, 2010): pp. 161-169.
Lahera, Vicente, et al. "Role of mitochondrial dysfunction in hypertension and besity." *Current hypertension reports* 19.2 (Feb. 23, 2017): pp. 1-9.
Moon, Hyo Eun et al. "Mitochondrial dysfunction in Parkinson's Disease." *Experimental neurobiology* 24.2 (Jun. 3, 2015): pp. 103-116.
Cao, Dedong, et al. "PGC-1α integrates glucose metabolism and angiogenesis in multiple myeloma cells by regulating VEGF and GLUT-4." *Oncology Reports* 31.3 (2014): pp. 1205-1210.
Wende, Adam R., et al. "PGC-1α coactivates PDK4 gene expression via the orphan nuclear receptor ERRα: a mechanism for transcriptional control of muscle glucose metabolism." *Molecular and cellular biology* 25.24 (Sep. 21, 2005): pp. 10684-10694.
Anwar, M., et al. Wahyuningsih. "Synthesis and characterization of dialkanolamides from castor oil (Ricinus communis) as nonionic surfactant." *IOP Conference Series: Earth and Environmental Science.* vol. 101. No. 1. IOP Publishing, (Oct. 23, 2017). pp. 1-6.
Grumati, Paolo, et al. "Autophagy in skeletal muscle homeostasis and in muscular dystrophies." *Cells* 1.3 (Jul. 26, 2012): pp. 325-345.
Martinez-Lopez, Nuria, et al. "Autophagy proteins regulate ERK phosphorylation." *Nature communications* 4.1 (Nov. 18, 2013): pp. 1-14.
Marseglia, Lucia, et al. "Oxidative stress in obesity: a critical component in human diseases." *International journal of molecular sciences* 16.1 (Dec. 26, 2014): pp. 378-400.
Peterson, Courtney M., et al. "Skeletal muscle mitochondria and aging: a review." *Journal of aging research* vol. 2012 (May 21, 2012): pp. 1-20.
Alway, Stephen E., et al. "Mitochondria initiate and regulate sarcopenia." *Exercise and sport sciences reviews* 45.2 (Apr. 1, 2018): pp. 58-69.
Johnson, Matthew L., et al. "Skeletal muscle aging and the mitochondrion." *Trends in endocrinology & metabolism* 24.5 (May 2013): pp. 247-256.
Liu, Jing, et al. "Reloading functionally ameliorates disuse-induced muscle atrophy by reversing mitochondrial dysfunction, and similar benefits are gained by administering a combination of mitochondrial nutrients." *Free Radical Biology and Medicine* 69 (Jan. 2, 2014): pp. 1-50.
Sandri, Marco, et al. "PGC-1α protects skeletal muscle from atrophy by suppressing FoxO3 action and atrophy-specific gene transcription." *Proceedings of the National Academy of Sciences* 103.44 (Sep. 13, 2006): pp. 16260-16265.
Novak, Elizabeth A., et al. "Mitochondrial dysfunction in inflammatory bowel disease." *Frontiers in cell and developmental biology* vol. 3 (Oct. 1, 2015): pp. 1-18.
Hom, Xenia B., et al. "Gastrointestinal complications of mitochondrial disease." *Mitochondrion* 4.5-6 (Jul. 12, 2004): pp. 601-607.
"Mitochondrial Myopathy Fact Sheet: what are mitochondrial myopathies?" National Institute of Neurological Disorders and Stroke https://www.ninds.nih.gov/Disorders/Patient-Caregiver-Education/Fact-Sheets/Mitochondrial-Myopathy-Fact-Sheet (Nov. 15, 2021) pp. 1-8.
Cohen, Bruce et al. "Dysautonomia" *United Mitochondrial Disease Foundation.*

\* cited by examiner

COMPOSITION FOR PROMOTING SKELETAL MUSCLE ACTIVITY VIA INDUCTION OF MITOCHONDRIAL BIOGENESIS COMPRISING OF AZELAIC ACID AS AN ACTIVE INGREDIENT

CROSS-REFERENCE TO RELATED APPLICATION

This application is a continuation in part of U.S. patent application Ser. No. 16/278,899 filed on Feb. 19, 2019 which claims priority to and the benefit of Korean Patent Application No. 10-2018-0020070, filed on Feb. 20, 2018, the disclosure of which is incorporated herein by reference in its entirety.

TECHNICAL FIELD

The following description relates to a composition for promoting mitochondrial biogenesis and for preventing, treating or improving a mitochondrial dysfunction-associated disease, including azelaic acid as an active ingredient.

BACKGROUND ART

Olfactory perception means that odorants bind to olfactory receptors (ORs) and are perceived by a brain through a signaling pathway. ORs, the largest protein family of G-protein coupled receptors (GPCRs), are proteins present in about 400 types in a human and involved in olfactory perception through a signaling pathway by binding to odorants in the olfactory epithelium. A recent study has reported that ORs are ectopically expressed in various tissues of a kidney, a liver, a small intestine, etc., as well as olfactory cells, but only a few OR functions are known.

Studies on biological efficacy of compounds included in foods and natural substances have primarily focused on non-volatile materials extracted with a polar/non-polar solvent, but studies on the biological functions of aromatic fragrance components, which are derived from volatile substances, are very limited except for some aromatherapy-related studies. According to the trends of recent studies, it has been reported that aromatic essential oils isolated from herbs such as the genus *Allium* have a strong antioxidant activity and are effective in controlling a lipid, blood sugar, and body fat (Fenwick G R et al.), but the molecular target of a single fragrance component has been little known.

The chemical name of azelaic acid is nonanedioic acid, which is a dicarboxylic acid having 9 carbon atoms. Azelaic acid is produced in a body through an omega-oxidation process, or as peroxide of linoleic acid, or ingested as a natural substance present in various cereals such as wheat, barley, oatmeal, sorghum, etc., and cranberries. Azelaic acid is naturally produced in a human body through fatty acid omega-oxidation. According to recent studies, it has been known that azelaic acid is effective against inflammatory dermal diseases such as redness, acne, etc., and some studies on atherosclerosis and anticancer activity have been reported, but detailed mechanisms such as the identification of a target protein have not been studied yet.

Recently, as it is known through various studies that mitochondrial dysfunction affects senescence as well as adult diseases such as diabetes and hypertension and chronic diseases such as Parkinson's disease and dementia, the importance of the maintenance of mitochondrial function is increasing.

The mitochondrion is an organelle primarily producing ATP, which is an energy source in cells, and has a variety of functions in cells such as metabolism, signal transduction, apoptosis, differentiation, etc. Mitochondria have mitochondrial DNA (mtDNA), which is distinguished from a cell's own nuclear DNA. Unlike nuclear DNA, mtDNA does not have a repair mechanism for repairing damage, and since there is no histone protein protecting DNA, it is relatively prone to damage. mtDNA damage leads to mitochondrial dysfunction, a decrease in synthesis of ATP, which is an energy source required for cell activity, and a decrease in ability to regulate homeostasis in a body, resulting in the onset of various diseases.

Endurance exercises such as running, swimming, etc. raise skeletal muscle respiratory capacity, which affects increase of enzymes involved in an electron transport chain, a citric acid cycle of mitochondria, and fatty acid oxidation. In addition, as a result of these endurance exercises, the size and number of mitochondria in skeletal muscle are increased as the rate of synthetic metabolism rather than the degradation metabolism of mitochondrial proteins increases. Therefore, since the improvement in oxygen utilization ability in skeletal muscle mitochondria improves ATP production capacity through oxidative phosphorylation, studies on mitochondrial biogenesis in skeletal muscle are very important in the research on improving exercise capacity.

The metabolic adaptation response in skeletal muscle is accomplished by regulating various genes, and the most critical factor in this response is a peroxisome proliferator-activated receptor-γ coactivator-1α (PGC-1α) transcription cofactor. PGC-1α plays a pivotal role in energy metabolism and mitochondrial biogenesis by being activated during exercise by upstream signaling mechanisms such as $Ca^{2+}$-regulated CAMKIV-calcineurin/NFAT and the MEF2 axis, adrenergic/cholinergic signaling, and AMP-activated protein kinase (AMPK). In addition, PGC-1α has been known to regulate mitochondrial biogenesis and expression of genes involved in sugar metabolism such as glucose transporter type 4, which is a blood sugar transporter, and pyruvate dehydrogenase kinase 4 (PDK4) inhibiting oxidation.

DISCLOSURE

Technical Problem

The inventors confirmed that Olfr544 is expressed in muscle cells, and azelaic acid acts as a ligand of Olfr544 in muscle cells to activate a CREB-PCG-1α pathway and an ERK1/2 signaling pathway, thereby inducing autophagy function of mitochondria, and increasing mtDNA and mitochondrial density.

Therefore, the present disclosure is directed to providing a composition for promoting mitochondrial biogenesis, which includes an azelaic acid as an active ingredient.

The present disclosure is also directed to providing a composition for preventing, treating or improving a mitochondrial dysfunction-associated disease, which includes an azelaic acid as an active ingredient.

The present disclosure is also directed to providing a composition for reinforcing muscle function or preventing muscle aging, which includes an azelaic acid as an active ingredient.

However, technical problems to be solved in the present disclosure are not limited to the above-described problems, and other problems which are not described herein will be fully understood by those of ordinary skill in the art from the following descriptions.

Technical Solution

To solve the above-described technical problems, the following description provides a composition for promoting mitochondrial biogenesis, which includes an effective amount of an azelaic acid or a pharmaceutically acceptable salt thereof as an active ingredient.

In an exemplary embodiment, the composition may activate Olfr544.

In another exemplary embodiment, the composition may increase expression of PGC-1α.

In still another exemplary embodiment, the composition may activate ERK1/2.

In addition, the following description provides a pharmaceutical composition for preventing or treating a mitochondrial dysfunction-associated disease, which includes an effective amount of an azelaic acid or a pharmaceutically acceptable salt thereof as an active ingredient.

The following description provides a food composition for preventing or improving a mitochondrial dysfunction-associated disease, which includes an effective amount of an azelaic acid or a pharmaceutically acceptable salt thereof as an active ingredient.

The following description provides a composition for reinforcing a muscle function or preventing muscle aging, which includes an effective amount of an azelaic acid or a pharmaceutically acceptable salt thereof as an active ingredient.

In an exemplary embodiment, the composition may reinforce a muscle function and prevent a muscle aging through activation of mitochondrial function.

In another exemplary embodiment, the composition may induce autophagy function of mitochondria in a cell.

In still another exemplary embodiment, the composition may promote mitochondrial biogenesis in a cell.

In yet another exemplary embodiment, the induction of the autophagy function and/or the promotion of biogenesis of the mitochondria may be caused by Olfr544 and ERK1/2 activation.

In addition, the following description provides a method of preventing or treating a mitochondrial dysfunction-associated disease, which includes administering an effective amount of an azelaic acid or a pharmaceutically acceptable salt thereof to a subject in need thereof.

In addition, the following description provides a method for preparing a drug for preventing or treating mitochondrial dysfunction-associated disease comprising an effective amount of an azelaic acid or a pharmaceutically acceptable salt thereof as an active ingredient.

In addition, the following description provides a method of reinforcing a muscle function or preventing muscle aging, which includes administering an effective amount of an azelaic acid or a pharmaceutically acceptable salt thereof to a subject.

In addition, the following description provides a method of treating a mitochondrial dysfunction-associated disease, which includes administering an effective amount of an azelaic acid or a pharmaceutically acceptable salt thereof to a subject in need thereof.

In addition, the following description provides a method for preparing a drug for reinforcing a muscle function or preventing muscle aging including an effective amount of an azelaic acid or a pharmaceutically acceptable salt thereof as an active ingredient.

In addition, the following description provides a method for preparing a drug for treating mitochondrial dysfunction-associated disease including an effective amount of an azelaic acid or a pharmaceutically acceptable salt thereof as an active ingredient.

Advantageous Effects

An azelaic acid is a compound mainly contained in cereals such as wheat, oats, barley, sorghum and natural products such as cranberries, etc. According to the following description, an azelaic acid induces mitochondrial autophagy and mitochondrial DNA synthesis in cells with the advantage of no or little side effects, thereby ultimately having activity of increasing mitochondrial density. Therefore, an azelaic acid can be used for the treatment of mitochondrial dysfunction-associated diseases associated with failure of homeostasis control of the mitochondria, for example, decrease of mitochondrial activity or decrease in the number of mitochondria. In addition, an azelaic acid can be used to reinforce a muscle function and prevent muscle aging due to the activities above, and can be effectively used in a food material, a pharmaceutical composition, and health functional foods for treating mitochondrial dysfunction-associated disease, reinforcing a muscle function, or preventing muscle aging.

DESCRIPTION OF DRAWINGS

Figure 5A:
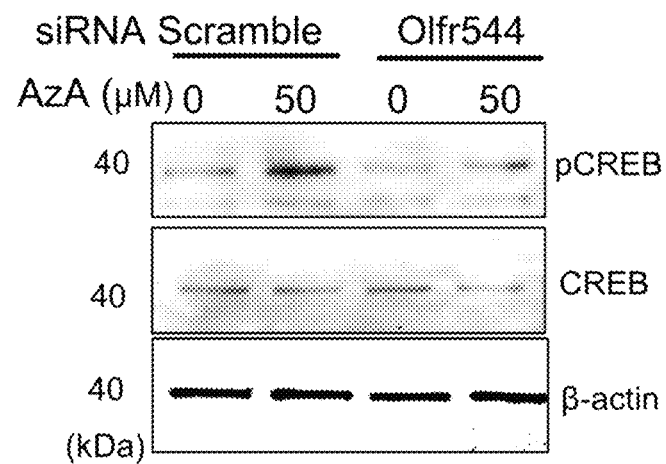
Figure 5B:
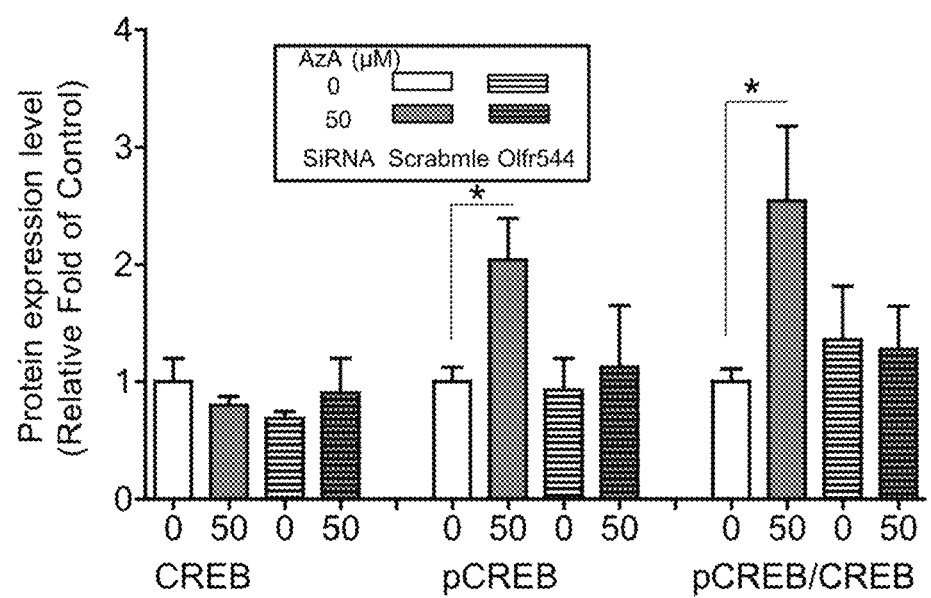
Figure 5C:
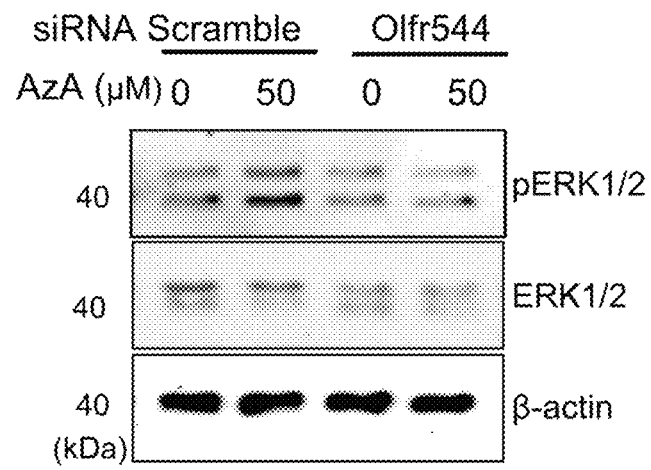
Figure 5D:
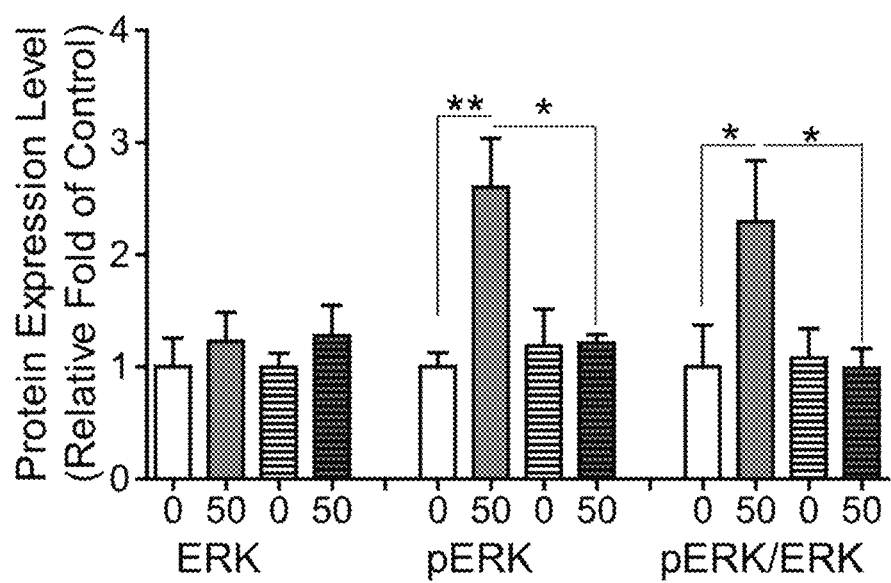
Figure 5E:
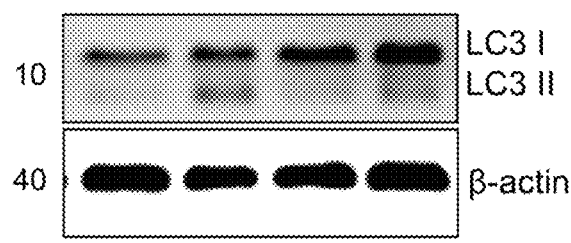
Figure 5F:
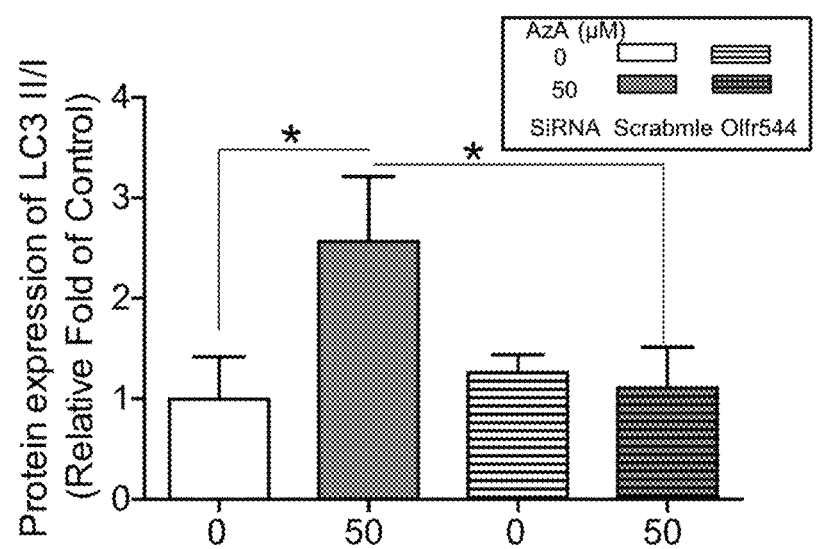

The above and other objects, features and advantages of the present disclosure will become more apparent to those of ordinary skill in the art by describing in detail exemplary embodiments thereof with reference to the accompanying drawings, in which:

FIG. 5A to FIG. 5F are diagrams showing mechanisms of promoting mitochondrial biogenesis according to Olfr544 activity of azelaic acid (FIG. 5A and FIG. 5B: analysis for pCREB and CREB protein expression, FIG. 5C and FIG. 5D: analysis for pERK1/2 and ERK1/2 protein expression, FIG. 5E and FIG. 5F: analysis for LC3 protein expression, according to an azelaic acid treatment in Olfr544 knockdown cells and normal cells).

Figure 6A:
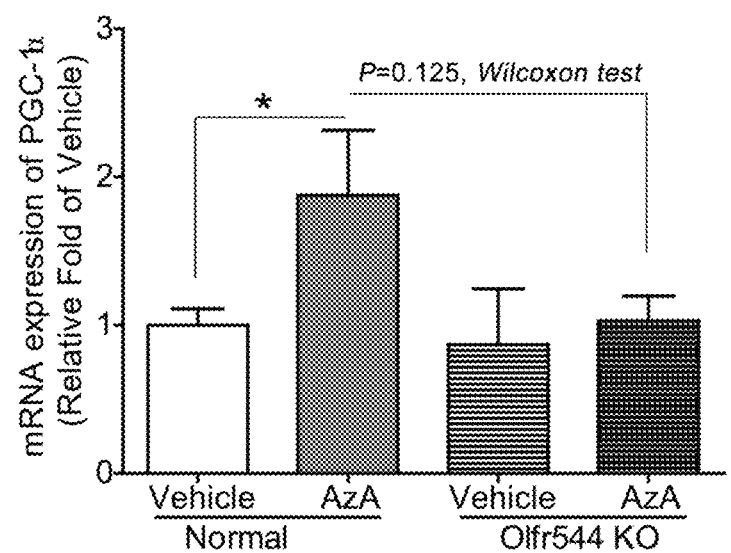
Figure 6B:
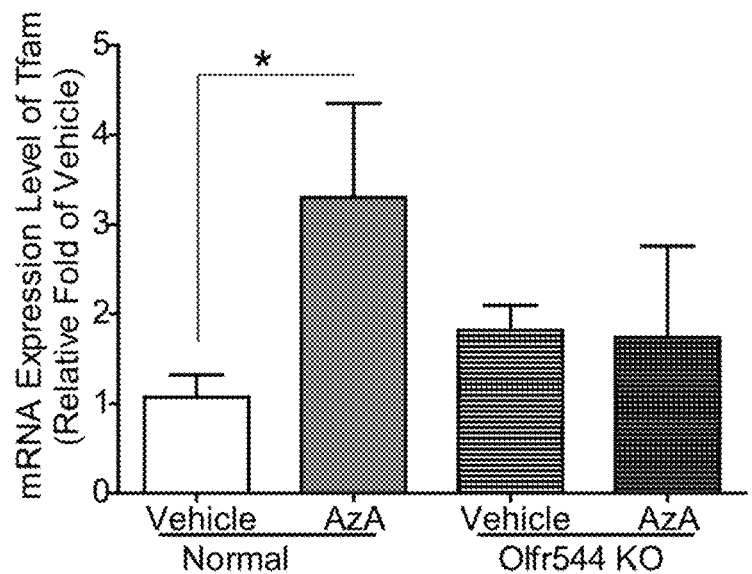
Figure 6C:
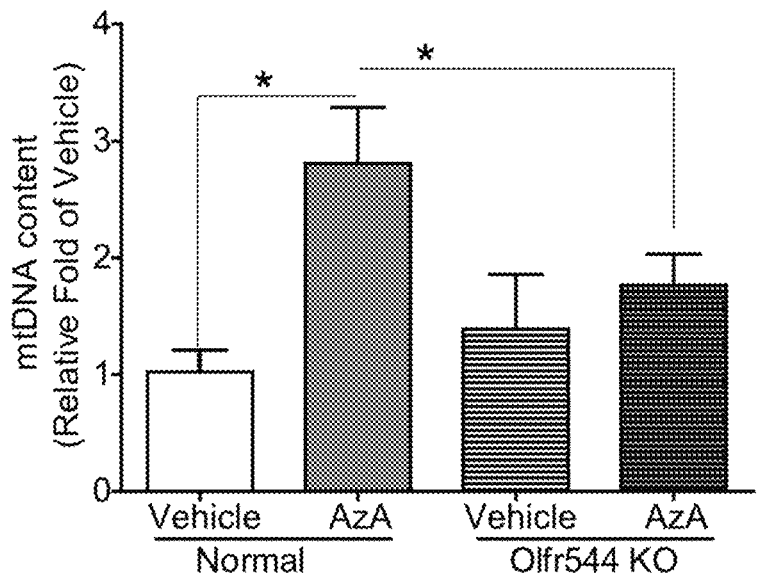

FIG. 6A to FIG. 6C are graphs showing an effect of increasing mitochondrial biogenesis according to administration of an azelaic acid to mice (FIG. 6A: analysis for PGC-1α gene expression level, FIG. 6B: analysis for Tfam gene expression level, and FIG. 6C: analysis for mtDNA expression level, when Olfr544 KO cells and normal cells are treated with an azelaic acid).

Figure 7A:
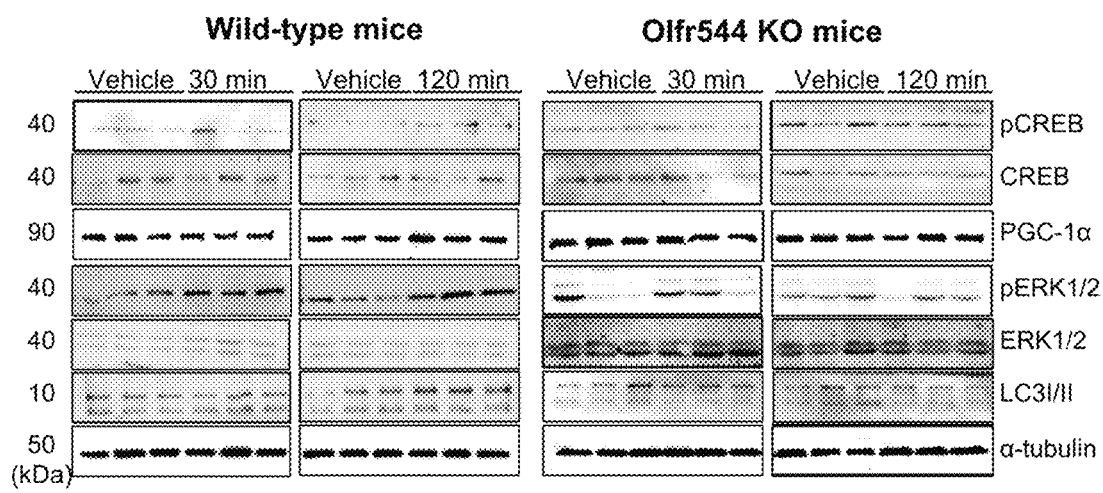
Figure 7B:
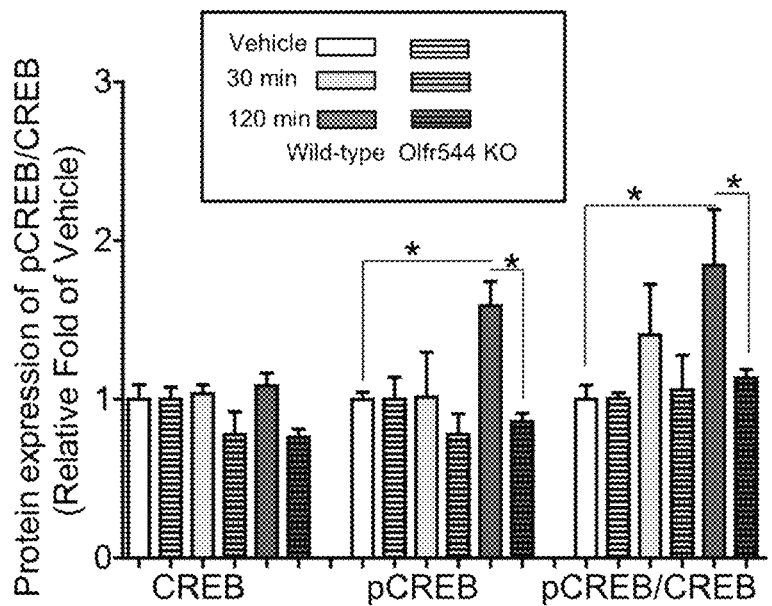
Figure 7C:
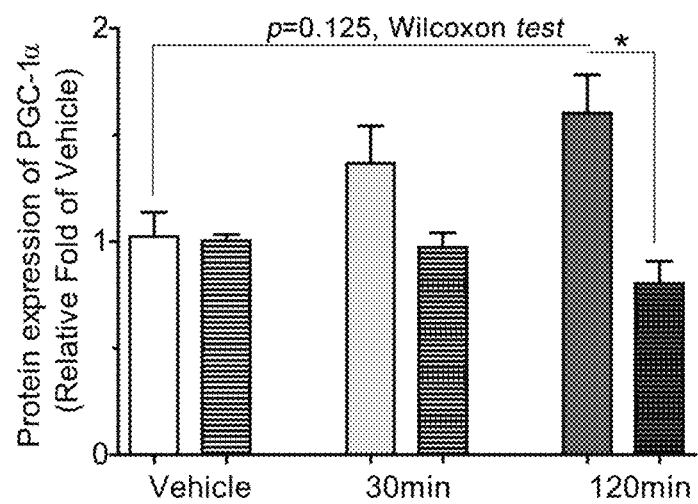
Figure 7D:
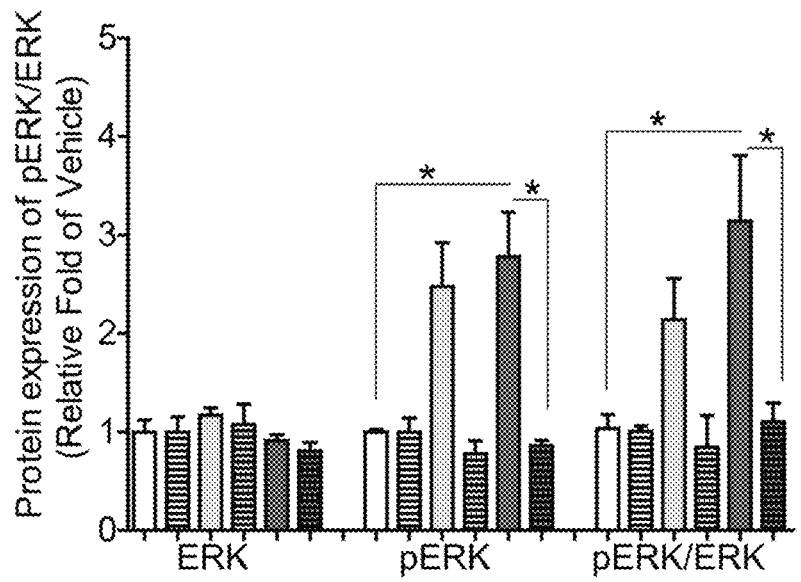
Figure 7E:
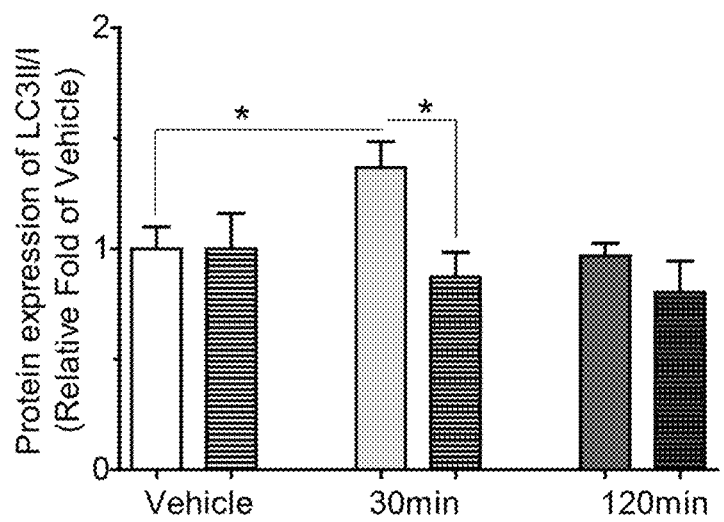

FIG. 7A to FIG. 7E are diagrams showing mechanisms of promoting mitochondrial biogenesis according to Olfr544 activity of an azelaic acid in mice (FIG. 7A: the images showing pCREB, CREB, PGC-1α, ERK1/2, pERK1/2 and LC3 proteins expression, FIG. 7B: analysis for pCREB and CREB protein expression levels, FIG. 7C: analysis for PGC-1α protein expression per an azelaic acid treatment time, FIG. 7D: analysis for pERK and ERK protein expression levels, and FIG. 7E: analysis for LC3 protein expression per an azelaic acid treatment time in muscle tissue extracted 30 and 120 minutes after an azelaic acid is intraperitoneally injected into normal mice and Olfr544 KO mice).

Figure 8:
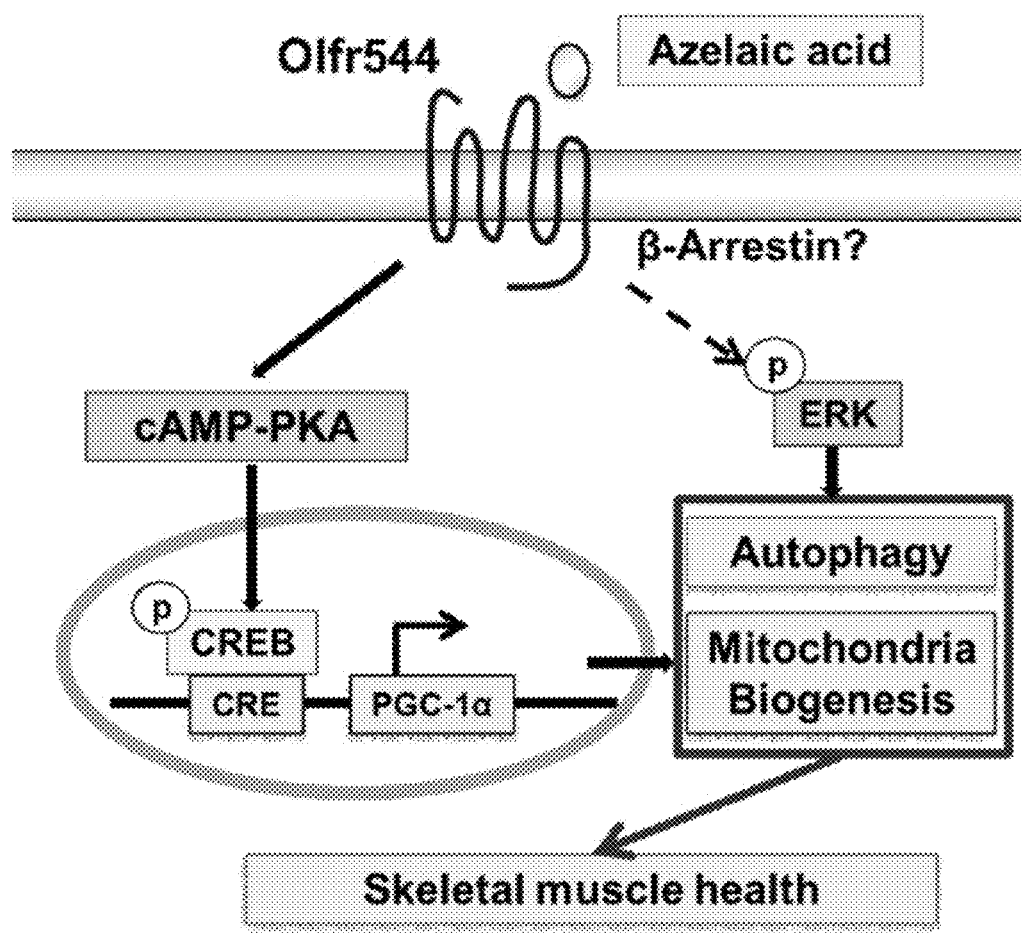

FIG. 8 is a schematic illustration proposing the mechanism by which azelaic acid-driven Olfr544 activation induces mitochondrial biogenesis in skeletal muscle cells by stimulation of CREB-PGC-1α signaling and ERK1/2 activity.

MODES OF THE DISCLOSURE

Exemplary embodiments of the present disclosure will be described in detail below with reference to the accompanying drawings. While the present disclosure is shown and described in connection with exemplary embodiments thereof, it will be apparent to those skilled in the art that various modifications can be made without departing from the spirit and scope of the claimed invention.

The inventors confirmed that an azelaic acid mainly contained in cereals such as wheat, oats, barley and sorghum and natural products such as cranberries, etc. increases mitochondrial biogenesis in muscle cells, and through a further study, confirmed that an azelaic acid functions as a ligand of Olfr544, which is a G-protein coupled receptor (GPCR), in muscle cells to activate an Olfr544-cAMP response element-binding protein (CREB)-PGC-1α pathway, and promotes mitochondrial biogenesis in cells by activating an ERK1/2 signaling pathway.

The term "azelaic acid (AzA)" used herein refers to nonanedioic acid, and has the structure of Formula 1, which has a molecular weight of 188.22 g/mol and a molecular formula of $C_9H_{16}O_4$.

[Formula 1]

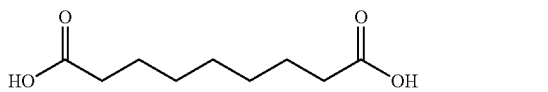

Since an azelaic acid is a compound mainly contained in cereals such as wheat, oats, barley and sorghum and natural products such as cranberries, etc. and has been known to be produced by omega oxidation of fatty acids in a human body, azelaic acid has an advantage of no or little side effects when administered to a subject. It was demonstrated that an azelaic acid present in a human body is safe for ingestion at a concentration of about 10 to 50 μM. In one exemplary embodiment of the present disclosure, as a result of evaluating the cytotoxicity of an azelaic acid through an MTT assay, it was observed that, even when a high concentration of an azelaic acid is treated, there is no change in cell viability, reconfirming safety of an azelaic acid (see Example 1).

Since the azelaic acid of the present disclosure is a natural substance and thus is not toxic, it can be continuously used in large quantities as an active ingredient for food or medicine.

The azelaic acid of the present disclosure may be obtained from cereals such as wheat, oats, barley and sorghum and natural products such as cranberries, etc. by a conventional extraction method such as juice extraction, vapor extraction, hot water extraction, ultrasonic extraction, solvent extraction or reflux cooling extraction. For example, for the extraction, one or more solvents selected from the group consisting of water, an alcohol having 1 to 4 carbon atoms, n-hexane, ethyl acetate, acetone, butyl acetate, 1,3-butylene glycol, methylene chloride, and a mixture thereof may be used, but the present disclosure is not limited thereto.

In addition, the azelaic acid of the present disclosure may be a synthetic compound, but such an azelaic acid can have the same efficacy as obtained from a natural product and can be used for the same purpose as that obtained from the natural product.

The inventors confirmed the efficacy of promoting mitochondrial biogenesis by an azelaic acid, which acts as a ligand of an olfactory receptor ectopically expressed in muscle cells. First, expression of olfactory receptor Olfr544 in muscle cells was confirmed, and an increase in mitochondrial biogenesis-related markers was confirmed when muscle cells were treated with an azelaic acid. Afterward, Olfr544 expression was artificially reduced using Olfr544 siRNA-treated cells and an Olfr544 knockout mouse, and compared to a control group. It was determined whether efficacy of the mitochondrial biogenesis of an azelaic acid is exhibited in an Olfr544-dependent manner.

More specifically, Olfr544 expression in muscle cells was confirmed (see Example 2), and also it was confirmed that mtDNA and mitochondrial density increase and expression of PGC-1α, which regulates mitochondrial functions, increases in response to the treatment of the muscle cells with an azelaic acid (see Example 3).

In addition, when Olfr544 knockdown myocytes, in which Olfr 544 expression is reduced by transforming Olfr544 siRNA, and normal cells are treated with an azelaic acid, PGC-1α expression, mtDNA and mitochondrial density increase in normal cells, but not in Olfr544 knockdown cells (see Example 4), suggesting that an azelaic acid serves as a ligand of Olfr544 in myocytes to induce Olfr544-dependent mitochondrial biogenesis.

Meanwhile, PGC-1α is a key element for mitochondrial function, and is considered as a master regulator of mitochondrial biogenesis and a strong coactivator of overactivation of a transcription factor affecting fatty acid oxidation and energy consumption in skeletal muscles in an entire body. In addition, PGC-1α is a coactivator of nuclear transcription factors such as nuclear respiratory factor-1 (NRF-1) and transcription factor A (TFAM), which are necessary for mitochondrial gene expression and genome replication.

In addition, in order to more specifically investigate a mitochondrial biogenesis mechanism of an azelaic acid in myocytes, the inventors confirmed change in expression levels of CREB/pCREB, EKR1/2 and LC3II/LC3I, when Olfr544 siRNA-transfected Olfr544 knockdown cells and normal cells are treated with an azelaic acid. As a result, unlike the Olfr544 knockdown cells, when normal cells are treated with an azelaic acid, expression of pCREB, pERK1/2 and LC3II/LC3I increases, and thus it can be seen that an azelaic acid promotes CREB-PGC-1α signaling and ERK1/2 activation in skeletal muscle tissue, and induces autophagy in the skeletal muscle cells (see Example 5).

Meanwhile, mitophagy refers to mitochondrial autophagy, and mitochondrial degradation by autophagy is a key mechanism of regulating mitochondrial homeostasis as well as mitochondrial biogenesis. Here, it has been known that, during exercise, autophagy prevents damage to mitochondria in skeletal muscle cells, improves adaptability of a muscle tissue, and plays a critical role in mitochondrial biogenesis. That is, proper level of autophagy is a key mechanism, which can inhibit aging of myocytes such that they can smoothly perform their function.

Accordingly, the azelaic acid of the present disclosure may induce mitochondrial autophagy in myocytes to prevent damage to mitochondria in skeletal muscle cells, improve muscle performance, increase a tissue ATP level, and promote mitochondrial biogenesis during exercise.

Therefore, the azelaic acid of the present disclosure may be used in prevention, treatment or improvement of mitochondrial dysfunction-associated disease.

The term "mitochondrial dysfunction-associated disease" used herein refers to various types of degenerative diseases, brain diseases, neurological diseases, heart diseases, liver diseases, kidney diseases, pancreatic diseases, metabolic diseases or muscle diseases, caused by failure of regulation of mitochondrial homeostasis such as a decrease in mitochondrial activity, a decrease in mitochondrial function, inappropriate mitochondrial activity, or a decrease in number of mitochondria. The degenerative disease may be degenerative arthritis, rheumatoid arthritis or osteoarthritis, the brain disease may be dementia, Parkinson's disease, stroke, developmental retardation, a neuropsychiatric disorder, a migraine, autism, mental retardation, seizures or stroke, the neurological disease may be ptosis, optic atrophy, strabismus, retinitis pigmentosa, blindness, hearing loss, eye muscle paralysis, hyporeflexia, syncope, nerve pain or autonomic imbalance, the heart disease may be a heart attack or cardiomyopathy, the liver disease may be hypoglycemia or hepatic insufficiency, the kidney disease may be nephrocalcinosis, the pancreatic disease may be pancreatic exocrine insufficiency or hypoparathyroidism, the metabolic disease may be hypertension, diabetes or obesity, and the muscle disease may be irritable bowel syndrome, muscular pain, muscular dystrophy, gastroesophageal reflux disease, hypotension, a convulsion or a motor disturbance, but the present disclosure is not limited thereto.

The composition of the present disclosure regulates mitochondrial homeostasis in cells, thereby promoting neuroprotective, neurotrophic, and/or neurite proliferation, and thereby improving cognitive function.

In addition, the composition of the present disclosure regulates mitochondrial homeostasis in cells to increase a metabolic rate, reduce a fat ratio, increase muscle mass, inhibit body weight gain or induce the decrease in body weight, improve mental ability (including memory), maintain or improve muscle performance, improve moods or manage stress, and thus can be effective in maintenance of the body and mental health of a subject.

According to the above, it can be seen that the azelaic acid of the present disclosure can reinforce muscle function and delay muscle aging through mitochondrial activation. The present disclosure provides a composition for reinforcing muscle function or preventing muscle aging, which includes an azelaic acid as an active ingredient, and includes, but is not limited to, a pharmaceutical composition, a plant composition, and a health functional food composition.

The term "muscle function" used herein refers to exerting a force for performing action, a force for maintaining posture, or generating heat for maintaining body temperature, by contraction, elasticity, excitability and conductivity of muscle fibers that constitute a muscle.

In addition, the term "muscle aging" used herein includes sarcopenia, and refers to a state, where muscle function is weakened as mitochondria in muscle fibers lose their activity, or the number of mitochondria decreases.

In an exemplary embodiment of the present disclosure, the inventors induced obesity in an Olfr544 knockout mouse and a normal mouse with a high-fat diet (HFD), respectively, and then an azelaic acid was orally administered to the Olfr544 knockout mouse and the normal mouse, thereby confirming that PGC-1α and Tfa expression increased in the normal mouse in response to the administration of the azelaic acid, and thus mtDNA increased. In addition, it was confirmed that, when azelaic acid was intraperitoneally administered, compared to the control group, pERK and LC3II/LC3I expression in the normal mouse increased (see Example 6). Therefore, it can be seen that the composition of the present disclosure is effective in prevention, treatment or improvement of obesity, particularly, induced by a high-fat diet.

In addition, the composition of the present disclosure includes azelaic acid as an active ingredient, and further includes one or more materials conventionally used to prevent or treat mitochondrial dysfunction-associated disease.

The term "prevention" used herein refers to all actions that delay the onset of a mitochondrial dysfunction-associated disease by administration of the pharmaceutical composition according to the present disclosure, the term "treatment" used herein refers to all actions that alleviate or beneficially change symptoms of a mitochondrial dysfunction-associated disease by administration of the pharmaceutical composition according to the present disclosure, the term "improvement" used herein refers to all actions that diminish parameters associated with a mitochondrial dysfunction-associated disease, for example, a degree of symptoms, by administration of the pharmaceutical composition according to the present disclosure.

In the present disclosure, an azelaic acid may be used in the form of a pharmaceutically acceptable salt, and as a salt, an acid-addition salt formed by a pharmaceutically acceptable free acid is preferable.

The term "salt" used herein is preferably an acid-addition salt formed by a pharmaceutically acceptable free acid. The acid-addition salt is obtained from an inorganic acid such as hydrochloric acid, nitric acid, phosphoric acid, sulfonic acid, hydrobromic acid, hydroiodic acid, nitrous acid or phosphorous acid; an aliphatic mono or dicarboxylate, a phenyl-substituted alkanoate, hydroxy alkanoate or alkandioate, an aromatic acid, or a non-toxic organic acid such as an aliphatic or aromatic sulfonic acid. Such pharmaceutically non-toxic salts include sulfates, pyrosulfates, bisulfates, sulfites, bisulfites, nitrates, phosphates, monohydrogen phosphates, dihydrogen phosphates, metaphosphates, pyrophosphates, chlorides, bromides, iodides, fluorides, acetates, propionates, decanoates, caprylates, acrylates, formates, isobutyrates, caprates, heptanoates, propiolates, oxalates, malonates, succinates, suberates, sebacates, fumarates, maleates, butyne-1,4-dioates, hexane-1,6-dioates, benzoates, chlorobenzoates, methyl benzoates, dinitrobenzoates, hydroxy benzoates, methoxy benzoates, phthalates, terephthalates, benzene sulfonates, toluenesulfonates, chlorobenzene sulfonates, xylene sulfonates, phenylacetates, phenylpropionates, phenylbutyrates, citrates, lactates, O-hydroxybutyrates, glycolates, malates, titrates, methanesulfonates, propane sulfonates, naphthalene-1-sulfonates, naphthalene-2-sulfonates, or mandelates.

The acid-addition salt according to the present disclosure may be prepared by a conventional method, for example, dissolving a compound represented by Formula 1 in an excessive amount of an acidic aqueous solution, and precipitating the salt using a water-miscible organic solvent, for example, methanol, ethanol, acetone or acetonitrile. Alternatively, the acid-addition salt according to the present disclosure may be prepared by evaporating the solvent or an excessive amount of acid from the mixture and then drying the resulting product, or suction-filtering the precipitated salt.

In addition, a pharmaceutically acceptable metal salt may be prepared using a base. An alkali metal or alkaline earth metal salt is obtained, for example, by dissolving a compound in an excessive amount of an alkali metal hydroxide or alkaline earth metal hydroxide solution, filtering a non-soluble compound salt, and evaporating and drying the filtrate. Here, as a metal salt, a sodium, potassium or calcium salt is preferable. The corresponding silver salt is obtained by reacting an alkali metal or alkaline earth metal with a suitable silver salt (e.g., silver nitrate).

In addition, the compound of the present disclosure includes all salts, isomers, hydrates and solvates, which can be prepared by conventional methods, as well as the pharmaceutically acceptable salt.

In the present disclosure, the pharmaceutical composition may further include suitable carrier, excipient and diluent, which are conventionally used in the preparation of a pharmaceutical composition.

The term "carrier" used herein is also called a vehicle, and means a compound that facilitates addition of a compound into cells or tissue. For example, dimethyl sulfoxide (DMSO) is a carrier conventionally used to facilitate input of various organic compounds into cells or tissue of an organism.

The term "diluent" used herein is defined not only as a compound which stabilizes a biologically active form of a target compound, but also as a compound which is diluted in a water dissolving the target compound. A salt dissolved in a buffer is used as a diluent in the art. A conventionally used buffer is phosphate buffered saline, and this is because it imitates a salt state of a human solution. Since the buffer salt can control the pH of a solution at a low concentration, the buffer diluent rarely modifies a biological activity of a compound. Compounds containing an azelaic acid, which are used herein, may be administered to a human patient by themselves, or in the form of a pharmaceutical composition in combination with other components or a suitable carrier or excipient, as used in combination therapy.

In addition, the pharmaceutical composition for preventing or treating a mitochondrial dysfunction-associated disease, which includes the azelaic acid according to the present disclosure, may be used in the form of a powder, a granule, a tablet, a capsule, a suspension, an emulsion, a syrup, an agent for external use, for example, an aerosol, or a sterile injection according to a conventional method, and carriers, excipients and diluents which can be included in the composition including an azelaic acid may be lactose, dextrose, sucrose, oligosaccharide, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate and mineral oil. The composition of the present disclosure may be formulated using a diluent or an excipient such as a filler, a thickening agent, a binder, a wetting agent, a disintegrant or a surfactant, which is conventionally used. A solid formulation for oral administration may be a tablet, a pill, a powder, a granule or a capsule, and such a solid formulation may be prepared by mixing at least one excipient, for example, starch, calcium carbonate, sucrose, lactose, and gelatin, with the active ingredient. Also, in addition to the simple excipient, lubricants such as magnesium stearate and talc may also be used. As a liquid formulation for oral administration, a suspension, a liquid for internal use, an emulsion, or a syrup may be used, and a conventionally-used simple diluent such as water or liquid paraffin, as well as various types of excipients, for example, a wetting agent, a sweetener, a fragrance, and a preservative may be included. A formulation for parenteral administration includes a sterilized aqueous solution, a non-aqueous solvent, a suspension, an emulsion, a lyophilizing agent and a suppository. As the non-aqueous solvent or suspension, propylene glycol, polyethylene glycol, vegetable oil such as olive oil, or an injectable ester such as ethyl oleate may be used. As a suppository base, Witepsol, Macrogol, Tween 61, cacao butter, laurin fat, or glycerogelatin may be used.

A therapeutically effective amount of the compound including the azelaic acid according to the present disclosure may be measured at an early stage of a cell culture assay. For example, a dose may be calculated in an animal model to obtain a circulation concentration range including a half maximal inhibitory concentration (IC50) or half maximal effective concentration (EC50), determined in cell culture. This information can be used to more exactly determine a useful dose in a human. A dose of the azelaic acid may be changed within the range according to an administration type and an administration route.

A preferable dose of the pharmaceutical composition of the present disclosure may vary according to a patient's condition and body weight, the severity of a disease, a formulation of a drug, an administration route and duration, and may be appropriately selected by one of ordinary skill in the art. However, for a preferable effect, the pharmaceutical composition of the present disclosure may be administered daily at 0.0001 to 1000 mg/kg, preferably 0.5 to 200 mg/kg, and more preferably 0.5 to 100 mg/kg. Administration may be performed one or several times per day. The dose does not limit the range of the present disclosure in any aspect.

The pharmaceutical composition according to the present disclosure may be administered to mammals such as a rat, a mouse, livestock, and a human by various routes such as parenteral administration, oral administration, and the like, and a route of administration may be expected, and the pharmaceutical composition according to the present disclosure may be administered, for example, orally, or by intrarectal, intravenous, intramuscular, subcutaneous, intrauterine dura mater or intracerebroventricular injection.

In addition, an oral formulation may vary according to a patient's age, sex or body weight, and may be administered at 0.1 to 100 mg/kg one to several times per day. In addition, the dose may be increased/decreased according to an administration route, a degree of a disease, sex, body weight, or age. Therefore, the dose does not limit the range of the present disclosure in any aspect.

In the present disclosure, when provided as a mixture containing other components in addition to an azelaic acid, the composition may include the azelaic acid at 0.001 to 99.9 wt %, preferably 0.1 to 99.0 wt %, and more preferably 30 to 50 wt % with respect to the total weight of the composition.

In addition, the present disclosure provides a food composition for preventing or improving a mitochondrial dysfunction-associated disease, which includes an azelaic acid as an active ingredient. In addition, the azelaic acid may be added to food for improving mitochondrial dysfunction-associated disease or vascular disease. When the azelaic acid of the present disclosure is used as a food additive, the azelaic acid may be added alone or in combination with another food or food component, and may be suitably used according to a conventional method. A mixing amount of the active ingredient may be suitably determined according to a purpose of use (prevention, health or therapeutic treatment). Generally, in manufacture of food or a drink, the azelaic acid of the present disclosure is added at 15 wt % or less, and preferably 10 wt % or less with respect to the raw components. However, in the case of long-term ingestion for health and hygiene or for health control, the amount may be less than the above range, and since there is no problem in terms of safety, the active ingredient may be used at an amount exceeding the above range.

In the present disclosure, the food includes functional food and health functional food, and the term "functional food" used herein means food improved in functionality compared to a general food by adding the azelaic acid of the present disclosure to the general food. The functionality may be classified into a physical property and physiological function, and when the azelaic acid of the present disclosure is added to the general food, the physical property and physiological function of the general food will be improved, and in the present disclosure, such food with the improved functions is defined overall as "functional food."

The functional food of the present disclosure may be used in various applications such as drugs, food, and drinks for preventing or improving a mitochondrial dysfunction-associated disease by regulating mitochondrial biogenesis and degradation in cells to maintain or improve the mitochondrial function, and increasing the number of mitochondria. There is no particular limitation to a type of food. Examples of food to which the material can be added include meats, sausages, breads, chocolate, candies, snacks, cookies, pizza, ramen, other types of noodles, gums, dairy products including ice creams, various types of soups, beverages, teas, drinks, alcohol drinks and vitamin complexes, and in a common sense, all types of food.

A health drink composition according to the present disclosure may contain various flavoring agents or natural carbohydrates as additional components like a conventional drink. The above-mentioned natural carbohydrates may include monosaccharides such as glucose and fructose, disaccharides such as maltose and sucrose, and polysaccharides such as dextrin and cyclodextrin, and sugar alcohols such as xylitol, sorbitol, erythritol, etc. As sweeteners, natural sweeteners such as thaumatin and a *stevia* extract, and synthetic sweeteners such as saccharin and aspartame may be used. A proportion of the natural carbohydrates is generally about 0.01 to 20 g, and preferably about 5 to 12 g per 100 mL of the composition of the present disclosure.

In addition to the components described above, the composition of the present disclosure may contain a variety of nutrients, vitamins, minerals (electrolytes), flavoring agents, pectic acid and a salt thereof, alginic acid and a salt thereof, organic acids, protective colloid thickening agents, pH modifiers, stabilizers, preservatives, glycerin, alcohol, or carbonating agents used in carbonated beverages. In addition, the composition according to the present disclosure may contain flesh for preparing natural fruit juices and vegetable juices. Such ingredients may be used independently or in combination. A ratio of such additive is not particularly limited, but generally selected in a range of 0.01 to 0.20 parts by weight with respect to 100 parts by weight of the composition of the present disclosure.

The present disclosure may have various modifications and embodiments, and thus the present disclosure will be described in further detail below. However, the present disclosure is not limited to specific embodiments, and it should be understood that the present disclosure includes all modifications, equivalents and alternatives included in the technical idea and scope of the present disclosure. To explain the present disclosure, if it is determined that a detailed description of the related art may obscure the gist of the present disclosure, the detailed description thereof will be omitted.

Hereinafter, to help in understanding the present disclosure, exemplary examples will be suggested. However, the following examples are merely provided to more easily understand the present disclosure, and not to limit the present disclosure.

EXAMPLES

Example 1. Evaluation of Cytotoxicity of Azelaic Acid

To evaluate cytotoxicity of an azelaic acid, an MTT assay was performed. The MTT assay is a test method utilizing the ability of mitochondria to reduce MTT tetrazolium, which is a yellow water-soluble substrate, to non-water-soluble MTT formazan showing a blue-violet color by a dehydrogenase. The MTT reagent was prepared by being diluted in phosphate buffered saline (PBS) at a concentration of 2 to 5 mg/mL. Hepa1c1c-7 cells used in this experiment were purchased from the Korean Cell Line Bank, and cultured in a minimum essential medium Eagle alpha modification medium (MEM-alpha, Hyclone) supplemented with 10% FBS and 1% PEST. For this experiment, the Hepa1c1c-7 cells ($4 \times 10^4$ cell/mL) were seeded into a 96-well plate and incubated at 37° C. under 5% $CO_2$ for 24 hours, and then incubated for 24 hours by adding an azelaic acid in a concentration range of 0 to 500 μM. Afterward, each sample was treated with 100 μL of the MTT reagent (4 mg/mL), incubated at 37° C. under 5% $CO_2$ for 4 hours and treated with 100 μL of dimethyl sulfoxide (DMSO), followed by measuring absorbance at 540 nm. Since the absorbance level is proportional to a cell count, a cell death effect caused by toxicity may be quantified.

Figure 1:
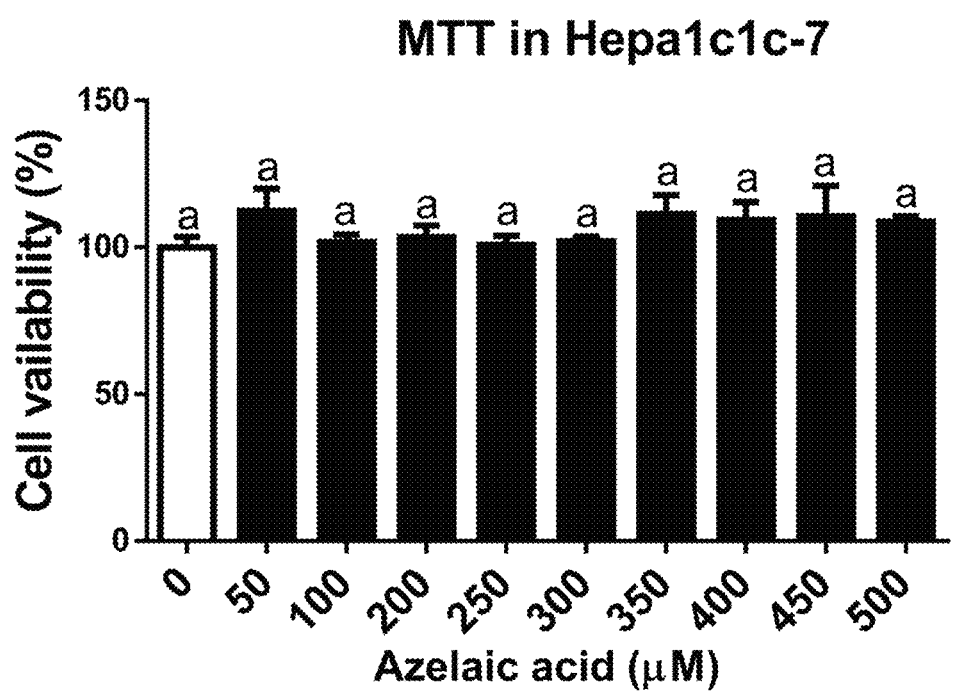
FIG. 1 is a diagram evaluating the cytotoxicity of an azelaic acid using an MTT assay.

As a result, as shown in FIG. 1, it was confirmed that, when the Hepa1c1c-7 cells were treated with 0 to 500 μM of azelaic acid, toxicity was not observed at any concentration compared to the control group.

Example 2. Confirmation of Olfr544 Expression in Muscle Cells and Murine Muscle 2-1. Cell Culture Murine skeletal muscle cells, C2C12 cells, were purchased from the Korean Cell Line Bank. The cells were cultured using a Dulbecco's modified Eagle's medium (DMEM) supplemented with 20% fetal bovine serum (FBS; HyClone, USA) and 1% antibiotics (penicillin/streptomycin). When the cells reached 50% confluency (the degree of proliferation) under 5% $CO_2$ (v/v) at 37° C., the cells were subcultured and maintained.

To differentiate the cells, the medium was replaced with DMEM containing 2% horse serum (HyClone), and after 7 days of differentiation, the cells were used in the experiment.

2-2. RT-PCR

RNA extracted from the murine skeletal muscle cells, C2C12 cells, was used to synthesize cDNA using the ReverTra Ace® qPCR RT Kit (TOYOBO, Osaka, Japan). RNA was pre-heated at 65° C. for 5 minutes and immediately stored on ice, to increase reaction efficiency. Afterward, a total of 8 μL of a reacting solution including 2 μl of 4× DN Master Mix including a gDNA remover, 0.5 μg of mRNA, and nuclease-free water was prepared, and amplification was carried out at 37° C. for 5 minutes. After the reaction, a 5×RT master mix was added to the reacting solution, and amplification was carried out at 37° C. for 15 minutes, 50° C. for 5 minutes, and 98° C. for 5 minutes, thereby synthesizing cDNA. The resulting PCR product was subjected to electrophoresis on an agarose gel, followed by imaging bands of the gel using ChemiDoc. As a control, L32 was used, and as a positive control, an Olfr544 plasmid was used.

2-3. Analysis of Results

Figure 2A:
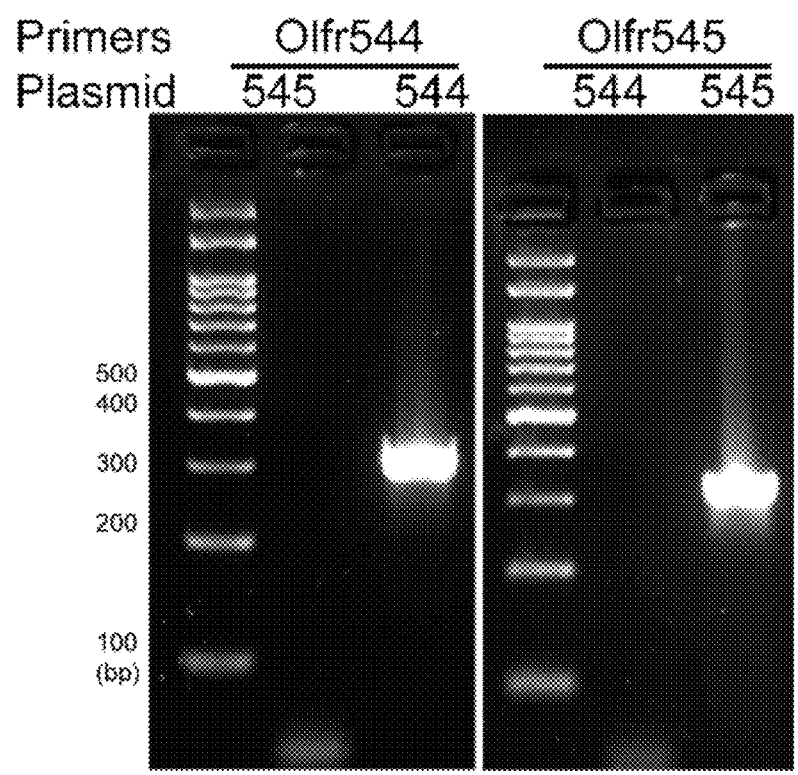
FIG. 2A and FIG. 2B are images for confirming the expression of an Olfr544 gene in muscle cells (FIG. 2A: confirmation of Olfr544 and Olfr545 plasmid expression, FIG. 2B: confirmation of Olfr544 and Olfr545 expression in myotubes, myocytes and muscle).
Figure 2B:
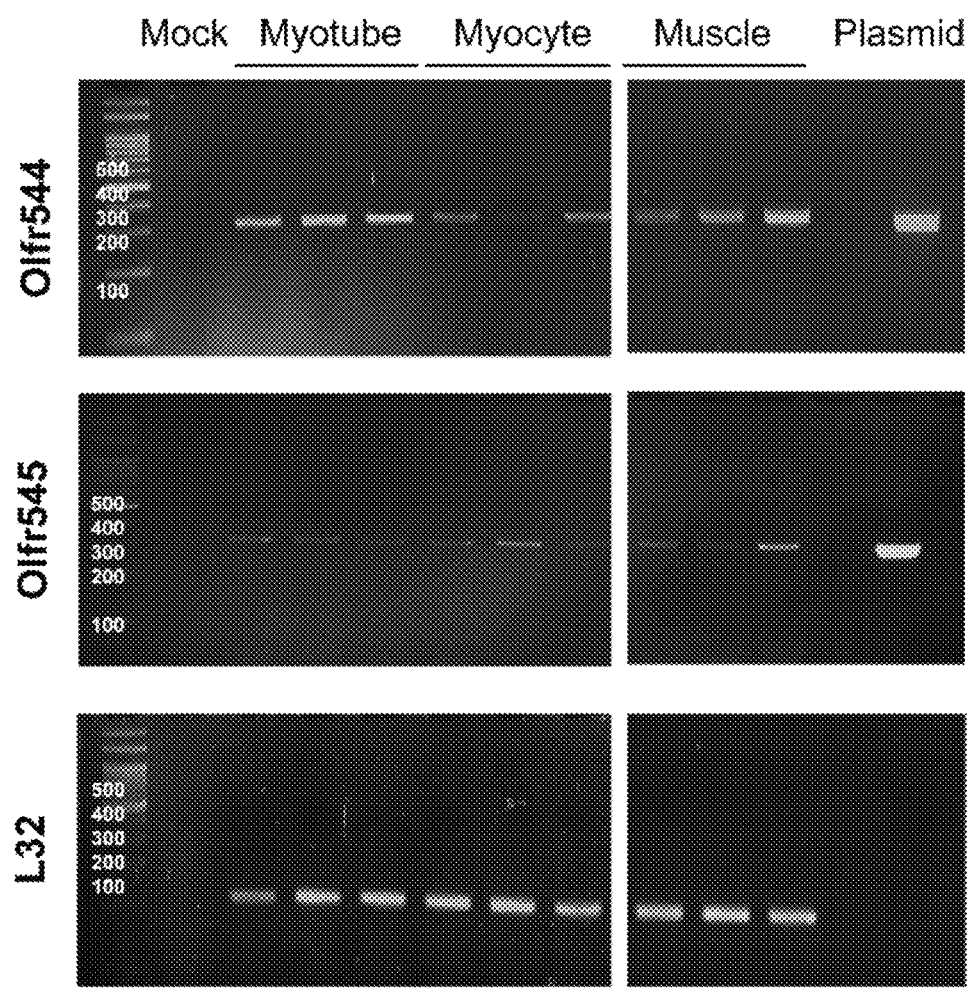
Figure 3A:
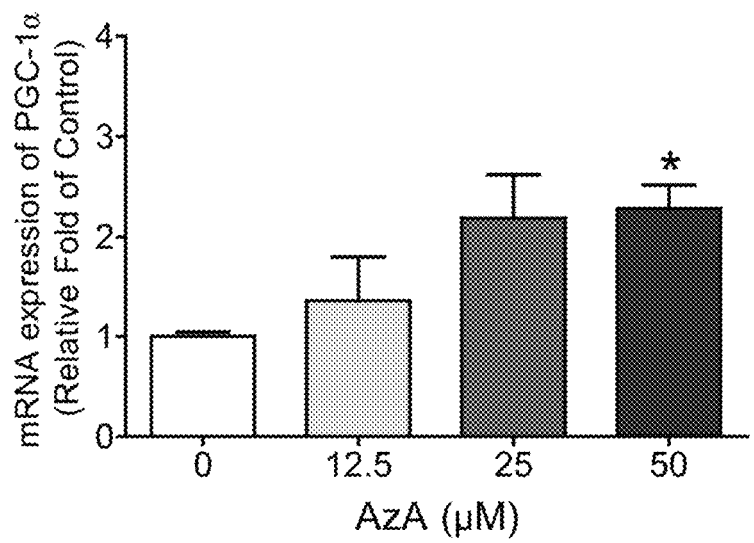
FIG. 3A to FIG. 3F are graphs and images showing a mitochondrial biogenesis promotion effect of an azelaic acid (FIG. 3A: analysis of PGC-1α gene expression according to azelaic acid, FIG. 3B: analysis of PGC-1α protein expression according to azelaic acid, FIG. 3C: analysis of mtDNA expression level according to azelaic acid, FIG. 3D: analysis of the change in mitochondrial density according to azelaic acid, FIG. 3E: density change according to azelaic acid, measured by immunofluorescence-based imaging, and FIG. 3F: the levels of mitochondrial content according to azelaic acid confirmed by confocal fluorescence microscopy; blue, nucleus; green, mitochondrion; Scale bar, 50 mm).
Figure 3B:
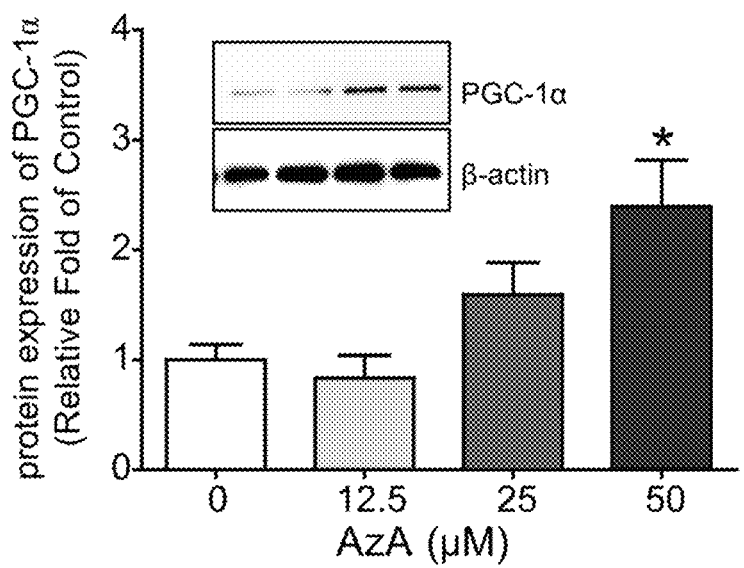
Figure 3C:
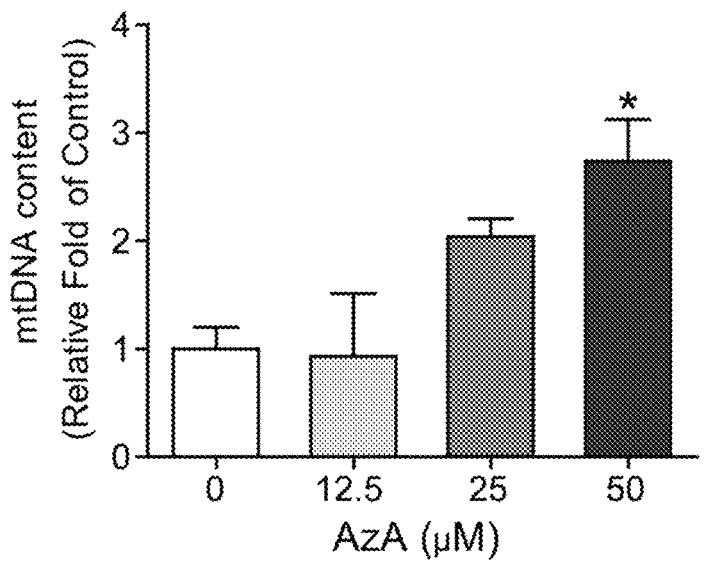
Figure 3D:
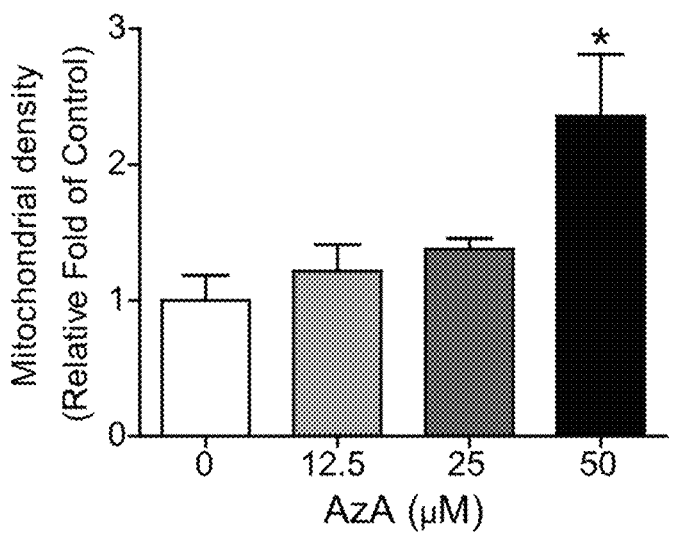
Figure 3E:
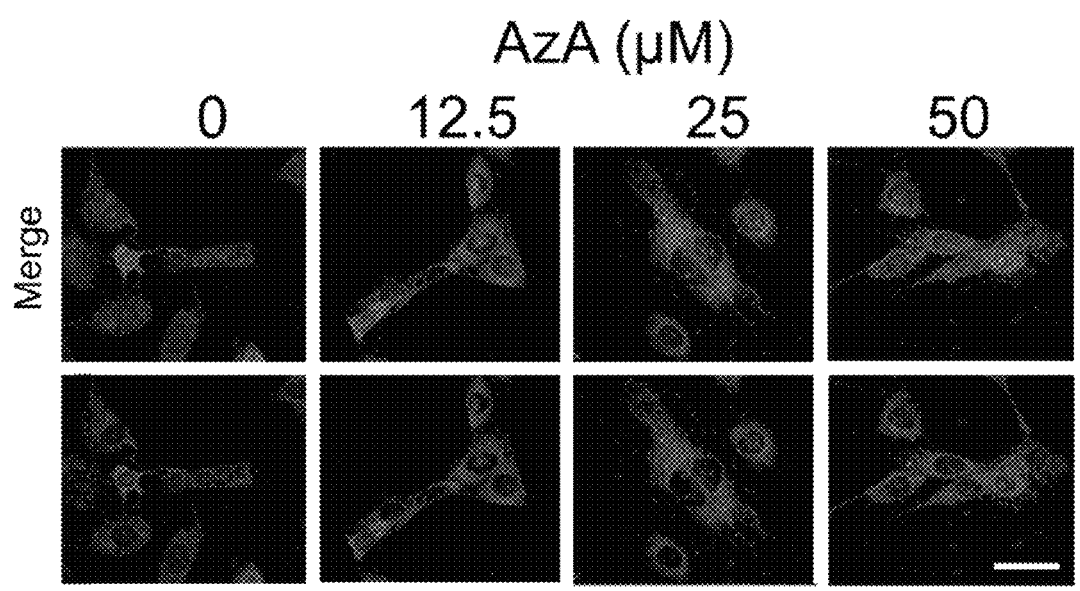
Figure 3F:
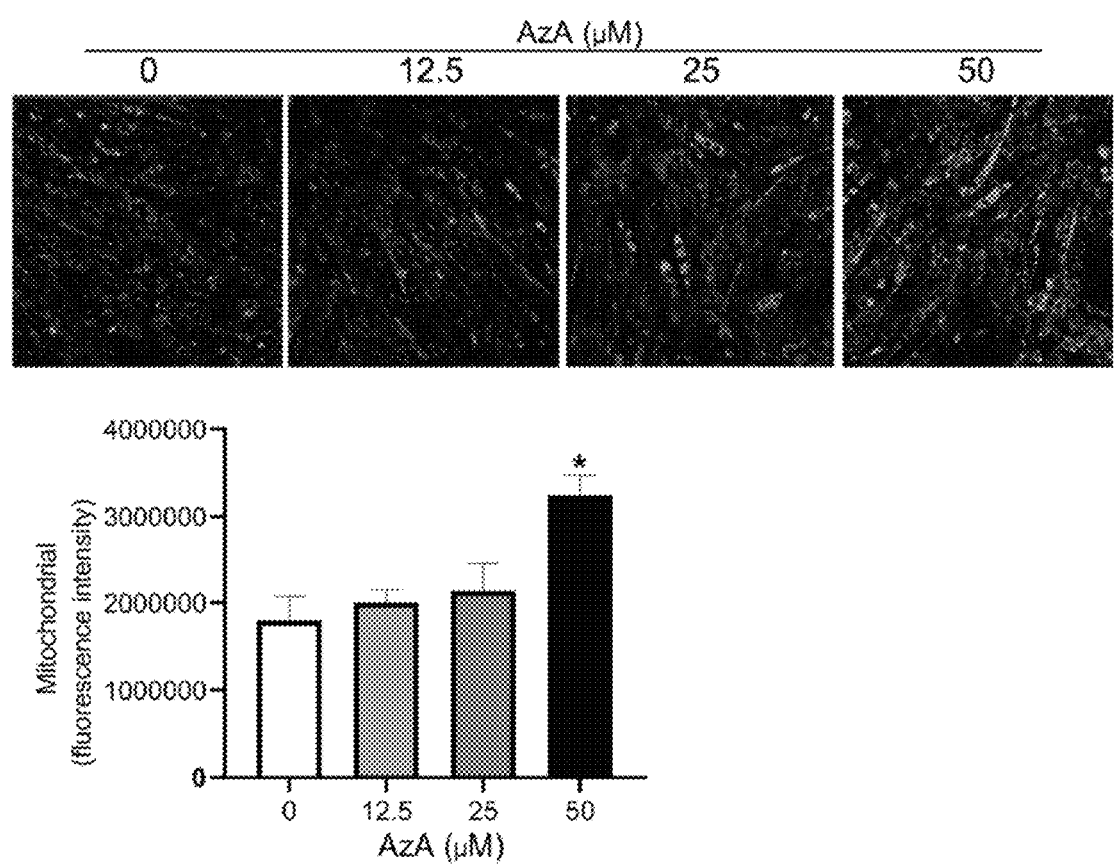
Figure 4A:
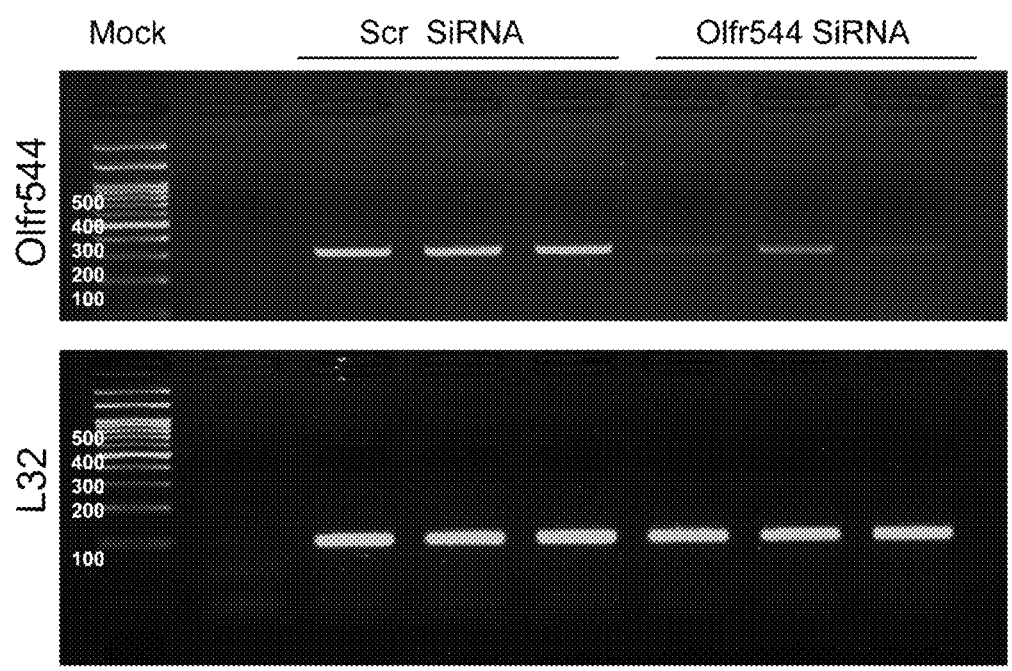
FIG. 4A to FIG. 4G are images showing the Olfr544-dependent mitochondrial biogenesis effect of an azelaic acid (FIG. 4A and FIG. 4B: confirmation of Olfr544 knockdown, FIG. 4C and FIG. 4D: analysis for PGC-1α expression at the mRNA and protein levels, FIG. 4E: analysis for mtDNA expression level, FIG. 4F: analysis for mitochondrial density, and FIG. 4G: fluorescence image for analysing mitochondrial abundance, in Olfr544 knockdown cells and normal cells).
Figure 4B:
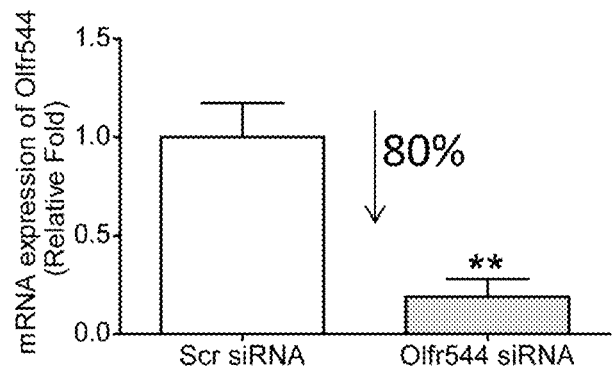
Figure 4C:
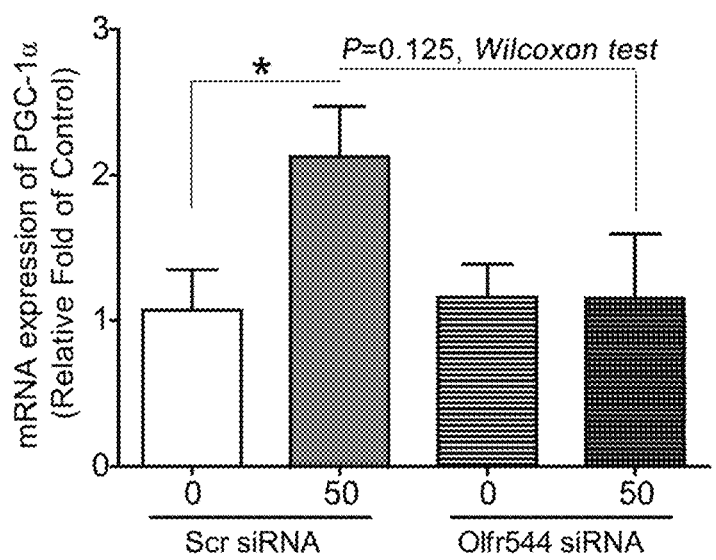
Figure 4D:
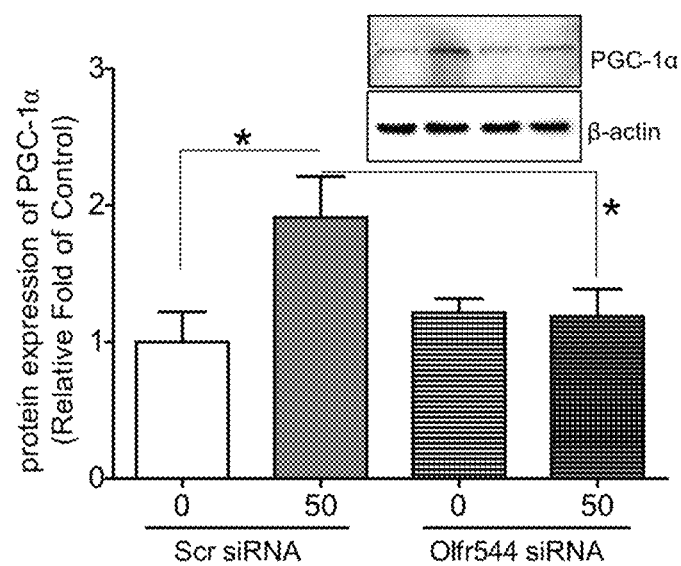
Figure 4E:
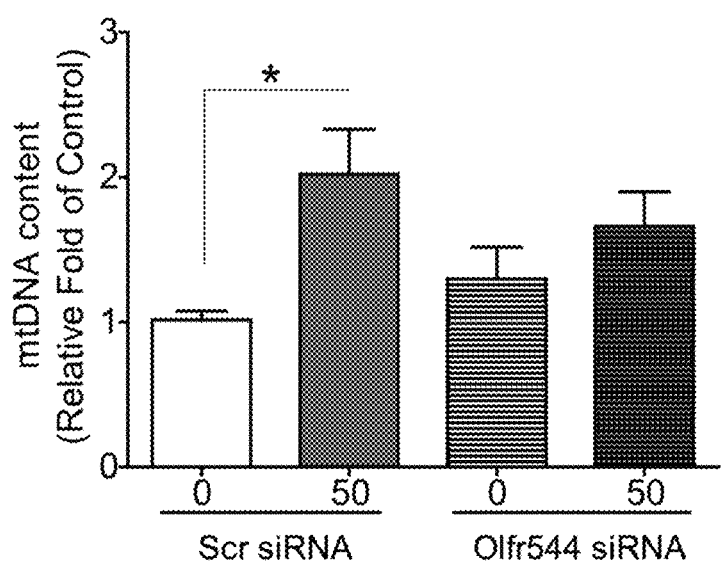
Figure 4F:
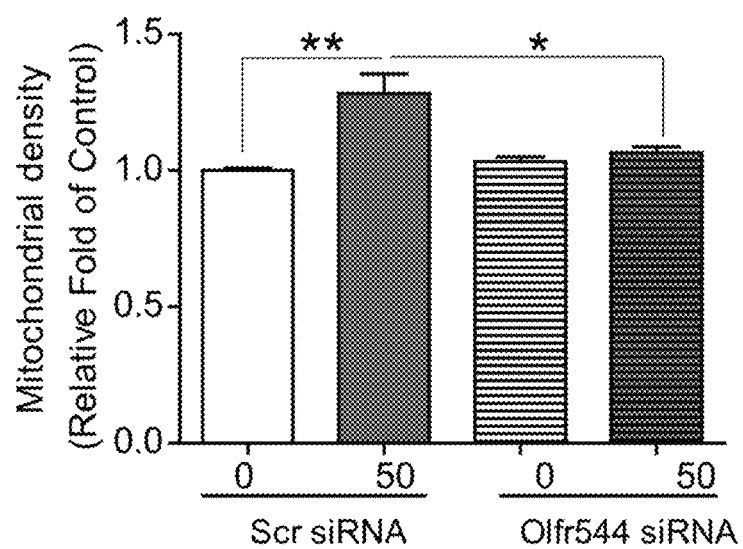
Figure 4G:
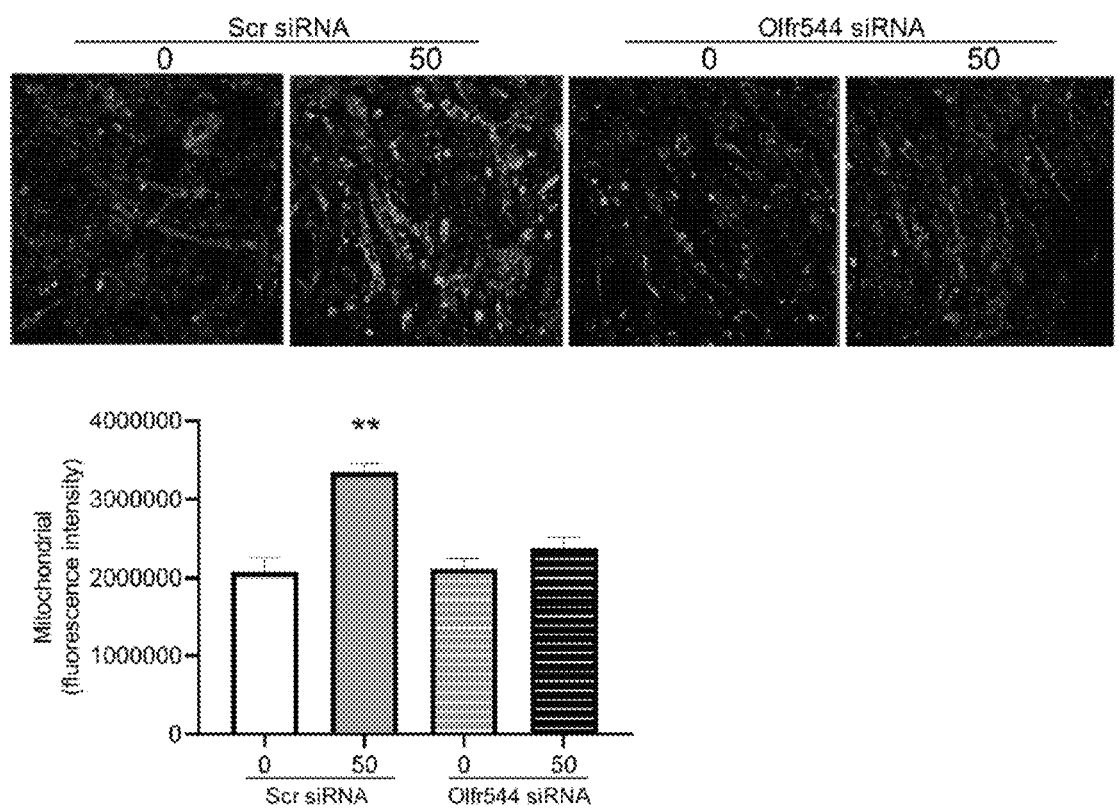

The results of RT-PCR performed to confirm whether Olfr544 is expressed in muscle is shown in FIG. 2.

As shown in FIG. 2, expression of the Olfr544 gene was confirmed in myotubes and myocytes, and also confirmed in murine muscle tissue (see B). Subsequently, as an olfactory receptor expressed in muscle cells was reconfirmed using Olfr545 having a similar gene sequence to Olfr544 (see A), it was confirmed that Olfr544 was expressed in muscle.

Based on the above results, the mitochondrial biogenesis efficiency in response to the azelaic acid treatment in muscle cells and murine muscle tissue was demonstrated.

Example 3. Confirmation of the Effect of Promoting Mitochondrial Biogenesis in Response to Azelaic Acid Treatment in Muscle Cells 3-1. Cell Culture and Treatment with Materials C2C12 cells differentiated for 7 days as described in Example 2-1 were treated with 12.5, 25 or 50 μM of an azelaic acid. After 24 hours, RNA and proteins were extracted according to the following method, and used in the experiment. For a control, instead of an azelaic acid, the same amount of DMSO was treated.

3-2. Quantitative Real-Time RT-PCR qPCR was performed to synthesize cDNA using RNA extracted from cells grown in a culture medium and then treated with 300 μL of the RNAiso plus reagent per well. Subsequently, the synthesized cDNA was subjected to qPCR using the Thunderbird TMSYBR® qPCR Mix reagent (Takara Bio Inc., Japan). A gene expression level was analyzed using the iQ5 Cycler System (Bio-Rad, USA).

3-3. Immunoblotting

Protein extraction was performed using an RIPA buffer (10 mM Tris-HCl, pH 7.5, 1% NP-40, 0.1% sodium deoxycholate, 0.1% SDS, 150 mM NaCl, and 1 mM EDTA), a Halt™ protease and a phosphatase inhibitor reagent (Thermo, USA). As primary antibodies, anti-α-tubulin (1:1000) and anti-PGC-1α (1:500; Santa Cruz Biotechnology, Santa Cruz, USA) were used. The resulting immunoblotting image was analyzed using the ChemiDoc™ touch imaging system and Image Lab 5.2 software (Bio-Rad, PA, USA).

3-4. MitoTracker

After treatment with azelaic acid, the change in mitochondrial density was detected using MitoTracker. C2C12 cells were treated with an azelaic acid for 24 hours, and then washed with PBS. Subsequently, a medium containing 200 mM of MitoTracker, i.e., a green probe, was added thereto, and the cells were cultured for 30 minutes. The mitochondrial density was measured by quantifying wavelengths of a part binding to the tracker, which absorbs a wavelength at 490 nm and emits a wavelength at 516 nm, using SpectraMax. Image analysis was performed using a confocal microscope and Zeiss LSM700 version 3.2 software (Carl Zeiss, Germany).

3-5. Analysis of Results

As shown in FIG. 3, when C2C12 cells were treated with the azelaic acid, expressions of PGC-1α gene and protein were increased in the 50 μM-treated group, compared to the control group (see A and B). Afterward, an mtDNA level and mitochondrial density were analyzed. As a result, it was confirmed that, in the 50 μM azelaic acid-treated group, the mtDNA level was increased about 2.5-fold higher than the control, and the mitochondrial density was significantly increased (see C and D). Subsequently, MitoTracker-probed mitochondrial images observed under confocal fluorescence microscopy showed substantial increases in mitochondrial density in the azelaic acid-treated group compared to the control group (see E and F). According to the above results, the treatment of a muscle cell line with an azelaic acid increased a major factor in regulating mitochondrial function, PGC-1α, and increased mitochondrial biogenesis, confirming that azelaic acid is effective in increasing mitochondrial biogenesis.

Example 4. Confirmation of Azelaic Acid Effect of Increasing Olfr544-Dependent Mitochondrial Biogenesis 4-1. siRNA Transfection The differentiated skeletal muscle cells, C2C12 cells, were transfected with 200 pmol of scramble (control) or Olfr544 siRNA duplex (Santa Cruz, USA) using the Lipofectamine 2000 reagent (Invitrogen, USA) for 6 hours. Subsequently, another transfection was performed for 10 to 12 hours. The transfected cells were used for RNA or protein extraction.

4-2. Quantitative Real-Time RT-PCR qPCR was performed to synthesize cDNA using RNA extracted from cells grown in a culture medium and then treated with 300 μL of the RNAiso plus reagent per well. Subsequently, the synthesized cDNA was subjected to qPCR using the Thunderbird TMSYBR® qPCR Mix reagent (Takara Bio Inc., Japan). A gene expression level was analyzed using the iQ5 Cycler System (Bio-Rad, USA).

4-3. Immunoblotting

Protein extraction was performed using an RIPA buffer (10 mM Tris-HCl, pH 7.5, 1% NP-40, 0.1% sodium deoxycholate, 0.1% SDS, 150 mM NaCl, and 1 mM EDTA), a Halt™ protease and a phosphatase inhibitor reagent (Thermo, USA). As primary antibodies, anti-α-tubulin (1:1000) and anti-PGC-1α (1:500; Santa Cruz Biotechnology, Santa Cruz, USA) were used. The resulting immunoblotting image was analyzed using the ChemiDoc™ touch imaging system and Image Lab 5.2 software (Bio-Rad, PA, USA).

4-4. Confirmation of Increased mtDNA Expression

The differentiated C2C12 cells were treated with azelaic acid, treated with 300 μL of a lysis buffer (20 mM EDTA, 100 mM Tris, 200 mM NaCl, 0.2% Triton X-100, 100 μg/mL) per well, and cultured at 37° C. for 90 minutes, and the extracted supernatant was treated with the same amount of isopropanol and 25 μL of a 4M NaCl solution. After storage at −20° C. overnight, distilled water (D.W.) was added to a pellet obtained by centrifugation (14,000 rpm, RT, 20 min), thereby extracting mtDNA. Afterward, 2 μl of DNA, 10 μl of the SYBR green PCR master mix, 0.5 μL of each of a forward primer and a reverse primer having a concentration of 10 pmol, and 6.6 μL of sterile distilled water were mixed, and qPCR was performed using the Thunderbird TMSYBR® qPCR Mix reagent (Takara Bio Inc., Japan). A gene expression level was analyzed using the iQ5 Cycler System (Bio-Rad, USA).

4-5. MitoTracker

The change in mitochondrial DNA content and abundance were determined using MitoTracker. Olfr544 siRNA-transfected cells were treated with an azelaic acid at a concentration of 50 μM for 24 hours, and then washed with PBS. Afterward, a medium containing 200 nM of the MitoTracker green probe was added to the cells, and the cells were cultured for 30 minutes. The mitochondrial density was measured by quantifying wavelengths of a part binding to the tracker, which absorbs a wavelength at 490 nm and emits a wavelength at 516 nm, using SpectraMax. The images were obtained by the Zeiss LSM700 confocal microscope, and then analyzed using the Zeiss LSM700 version 3.2 software (Carl Zeiss, Germany)

4-6. Analysis of Results

The experimental results are shown in FIG. 4. As a result of confirming Olfr544 expression in normal cells and Olfr544 knockdown cells by RT-PCR, it was confirmed that, compared to a Scr siRNA-transfected control, Olfr544 expression was decreased by about 80% in Olfr544 knockdown cells (see A and B), and then an experiment was carried out as follows. As a result of confirming the PGC-1α mRNA and protein expression in response to the azelaic acid treatment in the normal cells and the Olfr544 knockdown cells, it was confirmed that treatment of Scr siRNA-transfected normal cells with 50 μM of azelaic acid significantly increases a PGC-1α at both the mRNA and protein levels (see C and D). It was confirmed that this effect is not shown in the Olfr544 knockdown cells. Similarly, in an experiments of confirming mtDNA and mitochondrial density, in the Olfr544 knockdown cells treated with the azelaic acid, there were no changes in mtDNA and mitochondrial density, whereas mtDNA was increased about 1.6-fold in the azelaic acid-treated normal cells (see E). Also, quantification of mitochondrial density showed the enrichment of mitochondria in cells stimulated with azelaic acid (50 mM) in C2C12, but not in Olfr544 knockdown C2C12 myotubes (see F and G). The results collectively demonstrates that azelaic acid stimulates muscle mitochondrial function via Olfr544 and induces mitochondrial biogenesis in an Olfr544-dependent manner.

Example 5. Identification of the Mechanism of Promoting Mitochondrial Biogenesis Through Olfr544 Activation Induced by Azelaic Acid Examples 3 and 4 showed that Olfr544 activity induced by azelaic acid promotes mitochondrial biogenesis, and subsequently, in this example, it is shown by what mechanism does azelaic acid exhibit the above-described effect.

The PGC-1α gene is regulated by a CRE promoter, and CREB activation leads to upregulation of PGC-1α translation. The following experiment was carried out on the assumption that Olfr544 activated by an azelaic acid promotes PKA-CREB signaling, suggesting that the azelaic acid induces PGC-1α expression in skeletal muscle cells.

5-1. siRNA Transfection

The differentiated skeletal muscle cells, C2C12 cells, were transfected with 200 pmol of scramble (control) or Olfr544 siRNA (Santa Cruz, USA) using the Lipofectamine 2000 reagent (Invitrogen, USA) for 6 hours. Subsequently, one more transfection was performed for 10 to 12 hours. After 24 hours, the transfected cells were treated with an azelaic acid and used for protein extraction.

5-2. Immunoblotting

Protein extraction was performed using an RIPA buffer (10 mM Tris-HCl, pH 7.5, 1% NP-40, 0.1% sodium deoxycholate, 0.1% SDS, 150 mM NaCl, and 1 mM EDTA), a Halt™ protease and a phosphatase inhibitor reagent (Thermo, USA). As primary antibodies, anti-CREB (1:250), anti-p-CREB (Ser133; 1:500), anti-β-actin (1:1000), anti-α-tubulin (1:1000), anti-ERK1/2 (1:500), anti-p-ERK1/2 (Thr53,54, 1:500), and anti-PGC-1α (1:500; Santa Cruz Biotechnology, Santa Cruz, USA) were used. In addition, anti-LC3B (1:500) was purchased from Novus Biologicals (Novus Biologicals, USA). The resulting immunoblotting image was analyzed using the ChemiDoc™ touch imaging system and Image Lab 5.2 software (Bio-Rad, PA, USA).

5-3. Analysis of Results

The experimental results are shown in FIG. 5. After Olfr544 knockdown cells and normal cells were treated with azelaic acid, a CREB activation effect by the expression of a pCREB protein was confirmed. It was confirmed that the pCREB expression was increased about 2-fold after the normal cells were treated with an azelaic acid, whereas there was no change in pCREB expression in the Olfr544 knockdown cells even by the azelaic acid treatment (see A and B). In addition, it can be confirmed that the expression of a phosphorylated ERK1/2 protein was increased 1.5-fold in skeletal muscle cells (see C and D). Since ERK1/2 phosphorylation is known to enhance autophagy, the expression of an autophagy marker, i.e., the LC3II/LC3I protein, was confirmed. As a result, the azelaic acid treatment induced an about 3-fold increase in expression of the LC3II/LC3I protein, compared to the control group, and this effect disappeared in the Olfr544 knockdown cells (see E and F). Autophagy prevents mitochondrial biogenesis and mitochondrial damage during exercise, and thus plays a pivotal role in adaptation and ability of muscle tissue with respect to prolonged exercise.

According to the above results, it can be seen that the Olfr544 activity induced by azelaic acid promotes CREB-PGC-1α signaling and ERK1/2 activity in skeletal muscle tissue, thereby inducing autophagy in the skeletal muscle cells.

Example 6. Confirmation of the Effect of Improving Mitochondrial Biogenesis According to the Administration of Azelaic Acid to Mouse It was reported that obesity reduces mitochondrial replication and function in skeletal muscle involved in cell oxidation stress, lipotoxicity, and diabetic conditions. Therefore, this example analyzes a beneficial effect of administration of an azelaic acid to the muscle tissue of a mouse in which obesity was induced by HFD.

6-1. Models for Animal Experiments 8-week-old ICR male rats and C57BL/6J were purchased from Samtako (Gyeonggi-do, Seoul), and Olfr544 knockout mice from which exon 2 (161-428 bp) of an Olfr544 gene was removed using a CRISPR-Cas9 system were purchased from Macrogen (Seoul, Korea). All animal experiments were carried out in accordance with the experimental method (Protocol No. KUIACUC-2016-97) approved by the Animal Experiment Ethics Committee at Korea University. In the breeding environment, a 12-hour light cycle, a room temperature of 25 to 31° C., and relative humidity of 60% to 60% were maintained. The mice were freely fed a 60% high-fat diet, and randomly divided into 4 groups (n=7, two groups for normal mice, and the other two groups for knockout (KO) mice). For exact Olfr544 activation, the mice were fasted overnight, and then intraperitoneally injected with an azelaic acid (100 mg/kg of body weight). For a control, the same amount of PBS was intraperitoneally injected. In an experiment for long-term administration of an azelaic acid, the azelaic acid was orally administered at a dose of 100 mg/kg of body weight. During the last week of the experimental period (6 weeks), the mice fasted for 16 hours were anesthetized and sacrificed. The collected muscle tissue was put into a freezing tube, immediately put into liquid nitrogen, and then stored at −80° C.

6-2. Quantitative Real-Time RT-PCR cDNA was synthesized using RNA extracted by adding the RNAiso plus reagent to murine muscle cells. Subsequently, the synthesized cDNA was subjected to qPCR using the Thunderbird TMSYBR® qPCR Mix reagent (Takara Bio Inc., Japan). A gene expression level was analyzed using the iQ5 Cycler System (Bio-Rad, USA).

6-3. Confirmation of Increased Expression of mtDNA

Murine muscle cells were treated with a lysis buffer (20 mM EDTA, 100 mM Tris, 200 mM NaCl, 0.2% Triton X-100, 100 μg/mL), and cultured at 37° C. for 90 minutes, and the extracted supernatant was treated with the same amount of isopropanol and 25 μL of a 4M NaCl solution. After storage at −20° C. overnight, distilled water (D.W.) was added to a pellet obtained by centrifugation (14,000 rpm, RT, 20 min), thereby extracting mtDNA. Afterward, 2 μl of DNA, 10 μl of the SYBR green PCR master mix, 0.5 μL of each of a forward primer and a reverse primer having a concentration of 10 pmol, and 6.6 μL of sterile distilled water were mixed, and qPCR was performed using the Thunderbird TMSYBR® qPCR Mix reagent (Takara Bio Inc., Japan). A gene expression level was analyzed using the iQ5 Cycler System (Bio-Rad, USA).

6-4. Analysis of Results

The results of oral administration of azelaic acid are shown in FIG. 6, and the intraperitoneal administration results are shown in FIG. 7.

First, as a result of the oral administration of an azelaic acid, for 6 weeks, to the mice in which obesity was induced by HFD, as shown in FIG. 6, body weight, blood sugar, triglycerides, and sugar tolerance were increased, and PGC-1α mRNA expression was increased about 1.9-fold in the azelaic acid-administered group, compared to the control group. In contrast, there were no changes in the Olfr544 knockout mice even by the azelaic acid administration (see A). In addition, Tfa gene expression involved in mitochondrial PGC-1α downstream signaling was increased about 3.3-fold in normal mice due to azelaic acid (see B). In the knockout mice, there was no change. In addition, in the normal mice groups, the azelaic acid-administered mice, compared to the non-administered mice, mt DNAs were increased, but there was no change in the Olfr544 knockout mouse group (see C).

Afterward, as a result of the intraperitoneal injection of azelaic acid, as shown in FIG. 7, 30 minutes and 120 minutes after the intraperitoneal injection, the protein expression of pERK/ERK was compared with the control, confirming that the protein expression of pERK/ERK was increased 2.5-fold/2.8-fold 30 minutes/120 minutes after the injection, respectively. The protein expression of LC3II/LC3I was increased 1.5-fold 30 minutes after the azelaic acid injection, but was not changed 120 minutes after the azelaic acid injection. In the Okfr544 knockout mice, there was no change regardless of the azelaic acid injection. This result shows that the Olfr544 activation by azelaic acid induces autophagy in muscle tissue.

Collectively, the set of data in the present disclosure demonstrate that azelaic acid stimulates mitochondrial biogenesis and mitochondrial contents in skeletal muscle tissues via activation of Olfr544 (See FIG. 8).

Example 7. Statistical Analysis

The data are shown as the means±SEM. To determine significance between two or multiple groups, Wilcoxon test and one-way ANOVA followed by Tukey's HSD test were used, respectively. Data are statistically significant different denoted by * for P≤0.05, ** for P≤0.01.

It should be understood by those of ordinary skill in the art that the above description of the present disclosure is exemplary, and the exemplary embodiments disclosed herein can be easily modified into other specific forms without departing from the technical spirit or essential features of the claimed invention. Therefore, the exemplary embodiments described above should be interpreted as illustrative and not limited in any aspect. Therefore, the scope of the disclosure is defined not by the exemplary embodiments described above, but by the claims and their equivalents, and all variations within the scope of the claims and their equivalents are to be construed as being included in the disclosure.

What is claimed is:

1. A method for inhibiting muscle aging, comprising:
   administering a composition comprising an effective amount of an azelaic acid or a pharmaceutically acceptable salt thereof as an active ingredient to a muscle cell of a subject orally, or by intrarectal, intravenous, intramuscular, subcutaneous, intrauterine dura mater or intracerebroventricular injection,
   wherein the inhibition of muscle aging is accomplished by promoting mitochondrial biogenesis in the muscle cell,
   wherein the method increases an expression of a peroxisome proliferator-activated receptor gamma coactivator 1 alpha (PGC-1α) in the muscle cell,
   wherein the azelaic acid or the pharmaceutically acceptable salt thereof functions as a ligand of Olfr544 in muscle cells, and
   wherein the azelaic acid is administered at a concentration of 50 μM.

2. The method according to claim 1, wherein the method induces autophagy of mitochondria in the muscle cell.

3. The method according to claim 1, wherein the method activates Olfactory receptor 544 (Olfr544) in the muscle cell.

4. The method according to claim 1, wherein the method is for improvement of a muscle disease selected from the group consisting of irritable bowel syndrome, muscular pain, muscular dystrophy, sarcopenia, gastroesophageal reflux disease, hypotension, a convulsion and a motor disturbance.

5. A method for promoting mitochondrial biogenesis in a muscle cell, comprising:
administering a composition comprising an effective amount of an azelaic acid or a pharmaceutically acceptable salt thereof as an active ingredient to the muscle cell of a subject orally, or by intrarectal, intravenous, intramuscular, subcutaneous, intrauterine dura mater or intracerebroventricular injection,
wherein the method is for an inhibition of muscle aging,
wherein the method increases an expression of a peroxisome proliferator-activated receptor gamma coactivator 1 alpha (PGC-1α) in the muscle cell,
wherein the azelaic acid or the pharmaceutically acceptable salt thereof functions as a ligand of Olfr544 in muscle cells, and
wherein the azelaic acid is administered at a concentration of 50 μM.

* * * * *